United States Patent [19]

Moffett

[11] 4,017,492
[45] Apr. 12, 1977

[54] AS-TRIAZINOBENZODIAZEPIN-1-ONES

[75] Inventor: Robert B. Moffett, Kalamazoo, Mich.

[73] Assignee: The Upjohn Company, Kalamazoo, Mich.

[22] Filed: Apr. 2, 1976

[21] Appl. No.: 672,995

[52] U.S. Cl. .................. 260/248 AS; 260/247.5 C; 424/249; 260/239 BD; 260/247.2 B; 260/268 BC; 260/295 F; 260/293.59; 260/326.34
[51] Int. Cl.² ...................................... C07D 253/08
[58] Field of Search .................. 260/248 AS, 247.4

[56] References Cited

UNITED STATES PATENTS

| 3,818,003 | 6/1974 | Szmuszkovicz | 260/248 |
|---|---|---|---|
| 3,901,881 | 8/1975 | Szmuszkovicz | 260/248 |
| 3,933,816 | 1/1976 | Szmuszkovicz | 260/248 |

Primary Examiner—John M. Ford
Attorney, Agent, or Firm—Hans L. Berneis

[57] ABSTRACT

Compounds of the formula IV:

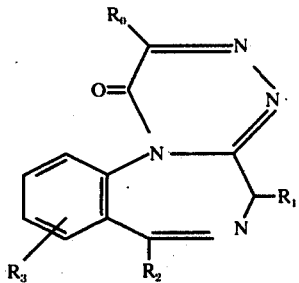

wherein $R_0$ is hydrogen, alkyl of 1 to 3 carbon atoms, inclusive, —$C_nH_{2n}OR$ in which $n$ is an integer of 1 to 3, inclusive, and R is hydrogen or methyl,

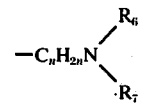

in which $n$ is defined as above, and $R_6$ and $R_7$ are hydrogen or alkyl as defined above, or together

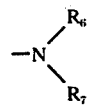

is pyrrolidino, piperidino, morpholino or

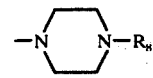

in which $R_8$ is methyl, ethyl, or 2-hydroxyethyl,

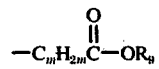

in which $m$ is an integer of 0 to 3, inclusive, and $R_9$ is hydrogen, lower alkyl of from 1 to 3 carbon atoms, inclusive, wherein $R_1$ is hydrogen or methyl; wherein $R_2$ is phenyl, o-chlorophenyl, o-fluorophenyl, 2,6-difluorophenyl, or 2-pyridyl; and wherein $R_3$ is hydrogen, fluoro, chloro, bromo, trifluoromethyl, or nitro.

The compounds of formula IV and the pharmacologically acceptable acid addition salts thereof have sedative, tranquilizing, anticonvulsive and muscle-relaxant activity and can thus be used to produce sedation and tranquilization in mammals, including man, and birds.

12 Claims, No Drawings

AS-TRIAZINOBENZODIAZEPIN-1-ONES

BACKGROUND OF THE INVENTION

1. Field of the Invention

This invention is directed to new organic compounds and is particularly concerned with novel compounds IV (substituted 7-phenyl-1,2-triazino[4,3-a][1,4[benzodiazepine-1(5H)-ones) and intermediates and a process for the production thereof.

The novel compounds and the process of production therefor can be illustratively represented as follows:

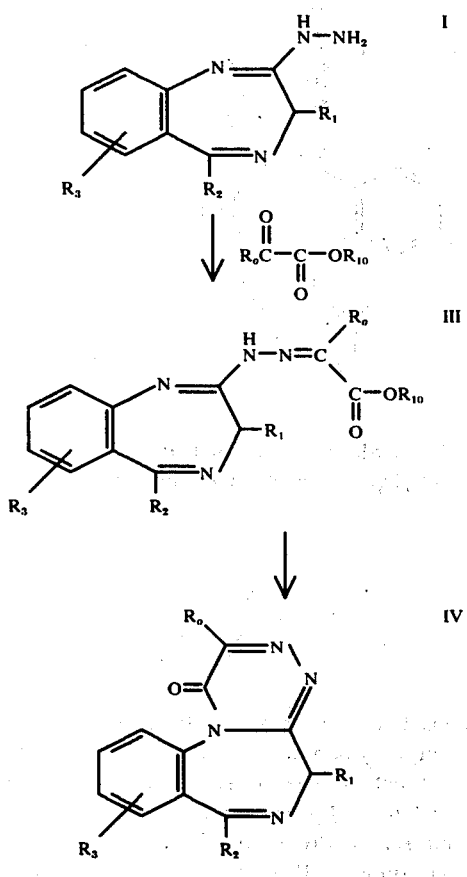

wherein $R_o$ is hydrogen, alkyl of 1 to 3 carbon atoms, inclusive, $-C_nH_{2n}OR$, in which $n$ in an integer of 1 to 3, inclusive, and R is hydrogen or methyl,

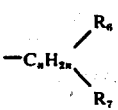

in which $n$ is defined as before and $R_6$ and $R_7$ are hydrogen or alkyl as defined above, or together

is pyrolidino, piperidino, morpholino, or

in which $R_8$ is methyl, ethyl, or 2-hydroxyethyl,

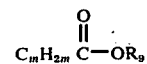

in which $m$ is an integer of 0 to 3, inclusive, and $R_9$ is hydrogen, lower alkyl of from 1 to 4 carbon atoms, inclusive, wherein $R_1$ is hydrogen or methyl; wherein $R_2$ is phenyl, o-chlorophenyl, o-fluorophenyl, 2,6-difluorophenyl, or 2-pyridyl; wherein $R_3$ is hydrogen, fluoro, chloro, bromo, trifluoromethyl, or nitro.

Alternatively, if in compound III, $R_9$ is hydrogen, then before cyclization, compound III can be converted to an imidazolide by treatment with a carbonyldiazolide (for example 1,1'-carbonyldiimidazole). This imidazolide will cyclize spontaneously or by heating to produce compound IV wherein $R_0$, $R_1$, $R_2$, and $R_3$ are defined as above.

The invention also embraces the pharmacologically acceptable acid addition salts of compound of formula III and IV.

The process of this invention comprises: reacting a 2-hydrazinobenzodiazepine compound of formula I with an α-ketocarboxylic acid or its ester (formula II) in an inert organic solvent at 10°–80° C. to obtain a compound of formula III. Compound III wherein $R_{10}$ is hydrogen can be converted to compound III wherein $R_{10}$ is lower alkyl by esterification (for example with a diazoalkane). Compound III can be converted to compound IV by heating in an inert or acidic solvent at a temperature of 25°–260°. If desired compound III wherein $R_{10}$ is hydrogen can be converted to the imidazolide and cyclized by heating in an inert solvent at a temperature between 0° and 100° C. to obtain compound IV.

Compounds IV, where $R_o$ is

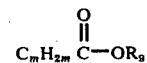

($m$ and $R_9$ as defined above) can be converted to compounds IV where $R_o$ is

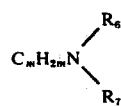

($m$, $R_6$ and $R_7$ as defined above) by the following processes:

1. When $R_0$ is $C_mH_{2m}COOH$ then this compound can be treated with diphenylphosphonylazide followed by rearrangement to the isocyanate, followed by hydrolysis to IV ($R_0 = C_mH_{2m}NH_2$) using procedures well known in the art for the Curtius or Schmidt reactions ["Organic Reactions" Vol. III, John Wiley and Sons, Inc. New York, NY., 1946, pages 307–451]. If desired IV ($R_0 = C_mH_{2m}NH_2$) can be alkylated in known manners.

2. IV ($R_0 = C_mH_{2m}COOH$) can alternately be converted to IV ($R_0 = C_mH_{2m}NH_2$) via the acid chloride, p-nitrophenyl ester or imidazolide then to the azide followed by rearrangement and hydrolysis as above.

Compounds IV in which $R_0$ is $C_nH_{2n}OH$ (n as defined above) can be treated with $SOCl_2$, $PBr_3$ or $ClSO_2R_{10}$ ($R_{10}$ = alkyl or aryl) and base to give IV ($R_0 = C_nH_{2n}Cl$, $C_nH_{2n}Br$ or $C_nH_{2n}OSO_2R_{10}$). This reactive intermediate can then be treated with

to give IV

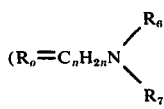

wherein $R_6$ and $R_7$ are defined above).

Compounds IV in which $R_0$ is $CH_3$ can be converted to IV in which $R_0$ is

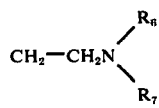

($R_6$ and $R_7$ as defined above except at least one $R_6$ or $R_7$ is not H) by the Mannich reaction which consists in treatment of IV ($r_0$= H) with formaldehyde and a primary or secondary amine

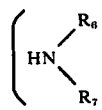

usually as an acid addition salt) or with

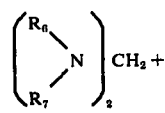

+ acetylchloride.

The procedures for the Mannich reaction are well known to those skilled in the art ["Organic Reactions", Vol. I, John Wiley and Sons, New York, NY., 1942, pages 303–341; ibid. Vol. VII, 1953, pages 99–197].

Compounds IV in which $R_0$ is $CH_3$ can be converted to IV in which $R_0$ is

($R_6$ and $R_7$ as defined above) by bromination followed by treatment with

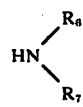

DESCRIPTION OF THE PREFERRED EMBODIMENT

Alkyl groups of 1 to 3 carbon atoms, inclusive, are exemplified by methyl, ethyl, and propyl.

The more preferred compounds are of the formula IVA:

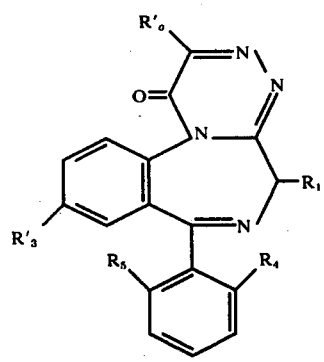

wherein $R'_0$ is hydrogen, alkyl of 1 to 3 carbon atoms, inclusive, —$C_nH_{2n}OH$, in which n is an integer of 1 to 3, or

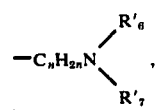

in which n is defined as above and $R'_6$ and $R'_7$ are alkyl of one to three carbon atoms, inclusive; wherein $R_1$ is hydrogen or methyl; wherein $R'_3$ is hydrogen, chloro, or fluoro; wherein $R_4$ is hydrogen, chloro, or fluoro; and wherein $R_5$ is hydrogen or fluoro with the proviso that $R_5$ is not fluoro, if $R_4$ is chloro, and the pharmacologically acceptable acid addition salts thereof.

The most preferred compounds are of the formula IVB:

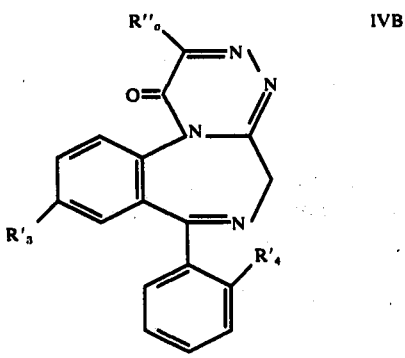

wherein $R''_0$ is hydrogen, methyl, hydroxymethyl, or

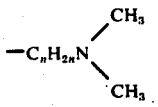

in which n is an integer of 1 to 3 inclusive; wherein $R'_3$ is hydrogen, chloro, or fluoro; and wherein $R'_4$ is hydrogen or chloro; and the pharmacologically acceptable acid addition salts thereof.

The novel compounds of the formula IV (and also IVA and IVB), have sedative, tranquilizing and muscle-relaxant effects in mammals and birds. Compounds of formula III beside being intermediates for the synthesis of compounds IV have also per se tranquilizing activity and can be used like compounds of formula IV.

Sedative effects of these compounds of formula IV (IVA and IVB included), were measured by standard procedures used in the art, and as shown below:

Chimney test: [Med. Exp. 4, 145 (1961)]: The test determines the ability of mice to back up and out of a vertical glass cylinder within 30 seconds. At the effective dosage ($ED_{50}$), 50% of the mice are unable to pass this test.

Dish test: Mice in Petri dishes (10 cm. diameter, 2 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice, including control (untreated) mice, are injected with nicotine salicylate (2 mg./kg.). The control mice show overstimulation, i.e., (1) running convulsions followed by (2) tonic extensor fits; followed by (3) death.

The pharmaceutical forms contemplated by this invention include pharmaceutical compositions suited for oral, parenteral and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, starch, stearic acid, methylcellulose, and the like may be used as carriers or for coating purposes. Water and oils, e.g., coconut oil, sesame oil, safflower oil, cottonseed oil, and peanut oil, may be used for preparing solutions or suspensions of the active drug. Sweetening, coloring, and flavoring agents may be added.

For mammals and birds food premixes, with starch, oatmeal, dried fishmeat, fishmeal, flour, and the like can be prepared.

As tranquilizer and anti-anxiety agents, the compounds of formulae IV (including IVA and IVB) can be used in dosages of 0.1 mg. to 5 mg./kg., preferably 0.2 to 3 mg./kg., in oral or injectable preparations as described above, to alleviate tension and anxiety in mammals, or birds, such as, e.g., occurs when animals are in travel. For larger animals, in excess of 5 kg. the lower-dosage ranges are indicated. Compounds of formula III can similarly be used but in dosages of 2–20 mg./kg.

The starting 2-hydrazino compounds of formula I can be prepared as shown by Kenji Meguro et al., Tetrahydron Letters, 47, 4039 (1970). This paper shows the preparation of compounds of formula I from (a) the 2-amino-5-phenyl-3H-1,4-benzodiazepine, (b) from the 2-methylmercapto-5-phenyl-3H-1,4-benzodiazepines and (c) from 5-phenyl-3H-1,4-benzodiazepine-2-thiones by heating either one of these compounds with hydrazine hydrate in methanol.

The necessary α-ketocarboxylic acids or esters II

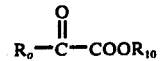

wherein $R_0$ and $R_{10}$ are defined as hereinbefore, are found in the literature including the necessary synthesis therefore, or if $R_0$ and $R_{10}$ are different from groups specifically described in the literature this compounds of formula II can be made by modified procedures obvious to one skilled in the art. Synthesis are disclosed by Archer et al., J. Am. Chem. Soc. 66, 1656 (1944); K. L. Waters, Chem. Rev. 41, 585 (1941); Fischer and Wieland, Chem. Ber. 93, 1387 (1960); Adickes et al., Am. Chem. 555, 41 (1944); Org. Synthesis Coll. Vol. I, 238, Vol, II, 53; Wright et al., J. Am. Chem. Soc. 77, 48–83 (1955); Igarashi et al., J. Org. Chem. 28, 3088 (1963) and ibid. 29, 2080 (1964); Libman and Kuznetsov, J. Gen. Chem. (USSR) 33, 1938 (1963).

In carrying out the process of this invention, a selected compound of formula I in an inert solvent is treated with a selected α-ketocarboxylic acid or its ester II at temperature of 0° to 80° C. As solvents, alkanols, such as methanol, ethanol, or 1- and 2-propanols, esters, such as diethylether, tetrahydrofuran or dioxane can be used. In the preferred embodiment of this invention the solvent is an alkanol with the same alkyl moiety as that of the ester reagent II used; the reaction is carried out at temperatures between 15° and 30° C. The time for this reaction in the preferred temperature range is from 2 to 48 hours. After the reaction is terminated, the product III is isolated and purified by conventional procedures such as evaporation of the reaction mixture, extraction, chromatography and crystallization.

Compound III is cyclized by heating it in an inert or acid solvent to a temperature of 25° to 260° C. Alternatively, if in a compound III $R_{10}$ is hydrogen, then, before cyclization, compound III may be converted to an imidazolide which will cyclize spontaneously or by heating. In the preferred embodiment of this invention solvents such as acetic acid, propionic acid, butyric acid, trifluoroacetic acid, 1,2,4-trichlorobenzene, indane, o-dichlorobenzene, cis-decaline, diethyleneglycol dimethyl or tetrahydrofuran, dioxane, tetralin, nitrobenzene, biphenyl, diphenyl ether, and the like or mixture thereof boiling in the above range can be used. A nitrogen atmosphere enhances the reaction. The time of the reaction is between 1 and 48 hours. After termination of the reaction product IV is recovered and purified by conventional procedures e.g. evaporation, extraction, chromatography, and recrystallization.

If the reagent II was the free acid, the resulting compound III in which $R_{10}$ is hydrogen is preferably first esterified for example with 3-methyl-1-p-tolyltriazine, diazomethane or the like or it may be converted to the imidazolide with 1,1'-carbonyldiimidazole prior to the cyclization.

EXAMPLE 1

7-Chloro-1-[[1-(methoxycarbonyl)ethylidene]-hydrazino]-5-phenyl-3H-1,4-benzodiazepine A mixture of 5.7 g. (0.02 mole) of 7-chloro-2-hydrazino-5-phenyl-3H-1,4-benzodiazepine, 3 ml. (0.04 mole) of methyl pyruvate and 50 ml. of methanol is stirred, under nitrogen, for 17 hours at room temperature, by which time the solid has dissolved. Three ml. more methyl pyruvate is added and the solution is allowed to stand for 7 hours more. After filtration and evaporation in vacuo (50° C./0.5 mm.) a brown gum is obtained which is chromatographed on silica gel and eluted with 1% methanol in chloroform. Evaporation of the combined fractions containing the product (as indicated by thin layer chromatography) gives a gum which is crystallized from a mixture of chloroform and ether. A yield of 3.5 g. (67%) of 7-chloro-2-[[1-methoxycarbonyl)ethylidene]hydrazino]-5-phenyl-3H-1,4-benzodiazepine is obtained as nearly white crystals of melting point 156°–157° C. Melt solvate indicates the product contained 1.95% $CHCl_3$ even after prolonged drying in vacuo.

Anal. calcd. for $C_{19}H_{17}ClN_4O_2 \cdot 0.06\ CHCl_3$: C, 60.88; H, 4.57; Cl, 11.12; N, 14.90; $CHCl_3$, 1.90. Found: C, 60.91; H, 4.48; Cl, 10.69; N, 15.09; $CHCl_3$, 1.95.

EXAMPLE 2

7-Chloro-1-[[1-(ethoxycarbonyl)ethylidene]-hydrazino]-5-phenyl-3H-1,4-benzodiazepine In the same manner given in Example 1, 7-chloro-2-hydrazino-5-phenyl-3H-1,4-benzodiazepine and ethyl pyruvate gives 7-chloro-2-[[1-(ethoxycarbonyl)ethylidene]hydrazino]-5-phenyl-3H-1,4-benzodiazepine as an oily product. NMR ($CDCl_3$) δ1.20 (t, 3, $CH_2CH_3$), 2.25 (2, 3, $CH_3$), 4.23 (q. 2, $CH_2CH_3$), 4.50 (broad s, 2, 3-$CH_2$), between 6.95 and 7.6 (m, 9, NH and arom H's).

EXAMPLE 3

7-Chloro-2-[(1-carboxyethylidene)hydrazino]-5-phenyl-3H-1,4-benzodiazepine

A mixture of 2.85 g. (0.01 mole) of 7-chloro-2-hydrazino-5-phenyl-3H-1,4-benzodiazepine and 0.847 ml. (0.012 mole) of pyruvic acid in 50 ml. of methanol under nitrogen is stirred at room temperature for 2.5 hours and then heated to the boiling point. The solid is dissolved by adding 50 ml. more methanol at the boiling point. On cooling the product cystallizes yielding 3.47 g. (97.6%) of 7-chloro-2-[(1-carboxyethylidene)-hydrazino]-5-phenyl-3H-1,4-benzodiazepine as a yellow-tan solid, of melting point 142°–165° C. (dec.). Recrystallization from methanol gives yellow crystals, of melting point 145°–165° C. (dec.) which are shown by nmr and melt solvate to contain 10.4% methanol of crystallization.

A 1.88 g. sample is dissolved in 25 ml. of ethyl acetate. Crystals start to separate almost immediately. After healing to boiling point and cooling the product is collected and dried giving 1.45 g. of 7-chloro-2-[(1-carboxyethylidene)hydrazino]-5-phenyl-3H-1,4-benzodiazepine of melting point 183°–185° C. (dec.).

Anal. calcd. for $C_{18}H_{15}ClN_4O$: C, 60.94; H, 4.26; Cl, 9.99; N, 15.79; Found: C, 60.99; H, 4.26; Cl, 9.95; N, 15.78.

EXAMPLE 4

7-Chloro-2-[[1-(methoxycarbonyl)ethylidene]-hydrazino]-5-phenyl-3H-1,4-benzodiazepine To a solution of 0.39 g. (0.001 mole) of 7-chloro-2-[(1-carboxyethylidene)hydrazino]-5-phenyl-3H-1,4-benzodiazepine is added 0.164 g. (0.0011 mole) of 3-methyl-1-p-tolyltriazene. After standing at room temperature (22°–25° C.) overnight, the solution is concentrated, then diluted with ether, filtered and evaporated to give a solid. This solid is redissolved in chloroform, diluted with ether and pentane to give .17 g. of 7-chloro-2-[[1-(merhoxycarbonyl)ethylidene]hydrazino]-5-phenyl-3H-1,4-benzodiazepine.

EXAMPLE 5

9-Chloro-2-methyl-7-phenyl-as-triazino[4,3-a]-[1,4]benzodiazepin-1(5H)-one

A solution of 0.76 g. (0.002 mole) of 7-chloro-2-[[1-methoxycarbonyl)ethylidene]hydrazino]-5-phenyl-3H-1,4-benzodiazepine in 25 ml. of 1,2,4-trichlorobenzene, under nitrogen is stirred under reflux (214° C.) for 8 hours. After filtration the solution is evaporated in vacuo and the residue is chromatographed on silica gel. Elution with 2% methanol in chloroform gives the desired product which is recrystallized from 2-propanol yielding 0.26 g. (38%) of 9-chloro-2-methyl-7-phenyl-as-traizino-[4,3-a][1,4]benzodiazepin-1(5H)-one of melting point 191.5°–193° C.

Anal. calcd. for $C_{18}H_{13}ClN_4O$: C, 64.20; H, 3.89; Cl, 10.53; N, 16.64. Found: C, 63.99; H, 4.23; Cl, 10.56; N, 16.26.

EXAMPLE 6

9-Chloro-2-methyl-7-phenyl-as-triazino[4,3-a]-[1,4benzodiazepin-1(5H)-one

A stirred solution of 0.37 g. (0.001 mole) of 7-chloro-2-[[1-(methoxycarbonyl)ethylidene]hydrazino]-5-phenyl-3H-1,4-benzodiazepine in 5 ml. of glacial acetic acid, under nitrogen, was refluxed for 45 minutes. The mixture was concentrated in vacuo and the residue mixed with $H_2O$, neutralized with $NaHCO_3$ and extracted with $CH_2Cl_2$. The extract was washed with water, saturated NaCl, dried ($Na_2SO_4$) and evaporated in vacuo. The residue is chromatographed on silica gel and eluted with 2% methanol-chloroform. The product thus isolated was evaporated in vacuo and the residue recrystallized from ethyl acetate-Skellysolve B hexane to give 0.18 g. (52%) of 9-chloro-2-methyl-7-phenyl-as-triazino[4,3-a][1,4]-benzodiazepin-1-(5H)-one of melting point 194°–196° C. The ir was identical to that prepared as in Example 5.

EXAMPLE 7

9-Chloro-2-methyl-7-phenyl-as-triazino[4,3-a]-[1,4]benzodiazepin-1(5H)-one

A stirred solution of 0.35 g. (0.001 mole) of 7-chloro-2-[(1-carboxyethylidene]hydrazino]-5-phenyl-3H-1,4-benzodiazepine in 5 ml. of glacial acetic acid, under nitrogen, was refluxed for 40 minutes. The mixture was concentrated in vacuo and the residue mixed with water, neutralized with $NaHCO_3$ and extracted with $CH_2Cl_2$. The extract was washed with water, saturated NaCl and dried (Na$_2$SO$_4$) and concentrated in vacuo. The residue was chromatographed on silica gel and eluted with 1% methanol-chloroform. The product thus isolated was evaporated in vacuo and the residue crystallized from EtOH-hexane to give 0.04 g. (12%) of 9-chloro-2-methyl-7-phenyl-as-triazino[4,3-a][1,4]-benzodiazpin-1(5H)-one of melting point 191°–194° C. The ir was identical to that prepared as in Example 5.

EXAMPLE 8

9-Chloro-2-methyl-7-phenyl-as-triazino[4,3-a]-[1,4]benzodiazepin-1(5H)-one

A. To a solution of 2.85 g. (0.01 mole) of 7-chloro-2-hydrazino-5-phenyl-3H-1,4-benzodiazepine in 100 ml. of tetrahydrofuran under nitrogen is added with stirring, 0.847 ml. (0.012 mole) of pyruvic acid. After 2.5 hours at room temperature and overnight at 0° C. 7-chloro-2-[(1-carboxyethylidene)hydrazino]-5-phenyl-3H-1,4-benzodiazepine is obtained.

B. To this solution of 7-chloro-2-[(1-carboxyethylidene)hydrazino]-5-phenyl-3H-1,4-benzodiazepine under nitrogen, is added with stirring, 50 ml. (0.015 mole) of an ethereal 0.3 molar solution of diazomethane. After 10 minutes the solution is evaporated giving 7-chloro-2-[[1-(methoxycarbonyl)ethylidene]-hydrazino]-5-phenyl-3H-1,4-benzodiazepine is obtained.

C. This ester is dissolved in 50 ml. of 1,2,4-trichlorobenzene and heated under nitrogen with stirring at reflux for 8 hours. After evaporation of the solvent the residue is chromatographed on silica gel and eluted with 2% methanol in chloroform. The combined fractions containing the product are evaporated and recrystallized from 2-propanol yielding 0.26 g. (7.7% overall yield) of 9-chloro-2-methyl-7-phenyl-as-triazino[4,3-a][1,4]-benzodiazepin-1-(5H)-one.

EXAMPLE 9

7-Chloro-2-[(1-carboxyethylidene)hydrazino]-5-(o-chlorophenyl)-3H-1,4-benzodiazepine, ethanol solvate To a mixture of 1.6 g. (0.005 mole) of 7-chloro-5-(o-chlorophenyl)-2-hydrazino-3H-1,4-benzodiazepine and 50 ml. of ethanol under nitrogen is added 0.5 mg. (0.007 mole) of pyruvic acid. A precipitate immediately separated. The mixture is warmed to the boiling point, cooled and stirred at room temperature for 2 hours. After standing in the refrigerator overnight the solid is collected, washed with ethanol and dried (1.5 hours at room temperature/0.02 mm.) giving 2.04 g. (94%) of 7-chloro- 2-[(1-carboxyethylidene)hydrazino]-5-(o-chlorophenyl)-3H-1,4-benzodiazepine, ethanol solvate of melting point 147°–151° C. (decomposition).

EXAMPLE 10

7-Chloro-2-[[1-(methoxycarbonyl)ethylidene]-hydrazino]-5-(o-chlorophenyl)-3H-1,4-benzodiazepine, methanol solvate To a solution of 4.35 g. (0.01 mole) of 7-chloro-2-[(1-carboxyethylidene)hydrazino -5-(o-chlorophenyl)-3H-1,4-benzodiazepine ethanol solvate in 300 ml. methylene chloride is added, dropwise, during 30 minutes 36.8 ml. (0.011 mole) of an 0.03 molar etheral solution of diazomethane. Removal of the solvent in vacuo leaves a residue which is crystallized from methanol yielding 3.1 g. (77.6%) of 7-chloro-2-[[1-(methoxycarbonyl)-ethylidene]hydrazino]-5-(o-chlorophenyl)-3H-1,4-benzodiazepine methanol solvate of melting point 109° C. dec. The ir spectrum is identical with that of Example 11.

EXAMPLE 11

7-Chloro-2-[[1-(methoxycarbonyl)ethylidene]-hydrazino]-5-(o-chlorophenyl)-3H-1,4-benzodiazepine, methanol solvate and 7-chloro-2-[(1-carboxyethylidene)-hydrazino]-5-(o-chlorophenyl)-3H-1,4-benzodiazepine, ethanol solvate To an ice-cooled mixture of 6.38 g. (0.02 mole) of 7-chloro-5-(o-chlorophenyl)-2-hydrazino-3H-1,4-benzodiazepine in 200 ml. of methanol is added dropwise 4.0 ml. of methyl pyruvate. The solution is removed in vacuo. The solid residue is diluted with ether and ice water and then made basic with sodium hydroxide. The etheral layer is separated, washed with water, dried over anhydrous sodium sulfate and evaporated. The resulting residue is crystallized from methanol to give 560 mg. (61.4%) of 7-chloro-2-[[1-(methoxycarbonyl)ethylidene]hydrazino]-5-(o-chlorophenyl)-3H-1,4-benzodiazepine, methanol solvate, m.p. 108°–127° C. (decomp.). Ir, nmr, and mass spectra support the structure, and nmr shows the presence of about 0.85 mole of methanol.

Anal. calcd. for C$_{19}$H$_{16}$Cl$_2$N$_4$O$_2$·0.85 CH$_3$OH C, 55.38; H, 4.54; Cl, 16.47; N, 13.01. Found: C, 54.68; H, 4.30; Cl, 16.49; N, 12.95.

The above cold basic aqueous solution, which is separated from the etheral phase is acidified with 2N hydrochloric acid. A precipitate forms which is collected by filtration, washed with water, and dried to give 5.38 g. (61.7%) of 7-chloro-2-[(1-carboxyethylidene)hydrazino]-5-(o-chlorophenyl)-3H-1,4-benzodiazepine m.p. 147°–163° C. (decomp). The material is recrystallized from 60% aqueous ethanol giving light yellow crystals of m.p. 147°–151° C. (dec). Ir, nmr, and mass spectrum support the structure, and nmr shows the presence of one mole of ethanol.

Anal. calcd. for: C$_{18}$H$_{14}$Cl$_2$N$_4$O$_2$·C$_2$H$_5$OH C, 55.18; H, 4.63; N, 12.87. Found: C, 55.11; H, 4.55; N, 12.64.

EXAMPLE 12

9-Chloro-7-(o-chlorophenyl)-2-methyl-as-triazino[4,3-a][1,4]benzodiazepin-1(5H)-one A solution of 4.5 g. (0.0113 mole) of 7-chloro-2-[[1-(methoxycarbonyl)ethylidene]hydrazino]-5-(o-chlorophenyl)-3H-1,4-benzodiazepine, methanol solvate in 125 ml. 1,2,4-trichlorobenzene is gently refluxed under nitrogen with a short air condenser for 10 hours. Removal of the solvent in vacuo gives a dark residue which is crystallized from ethyl acetate giving 1.93 g. (47.0%) of 9-chloro-7-(o-chlorophenyl)-2-methyl-as-triazino[4,3-a][1,4]benzodiazepin-1(5H)-one of melting point 211.5°–213° C. Ir, nmr, and mass spec support the structure.

Anal. calcd. for: C$_{18}$H$_{12}$Cl$_2$N$_4$O: C, 58.24; H, 3.26; Cl, 19.10; N, 15.09. Found: C, 58.46; H, 3.45; Cl, 18.84; N, 15.00.

EXAMPLE 13

7-Chloro-2-[[1-carboxy-4-(diethylamino)-butylidene]-hydrazino]-5-phenyl-3H-1,4-benzodiazepine To a stirred solution of 2.85 g. (0.01 mole) of 7-chloro-2-hydrazino-5-phenyl-3H-1,4-benzodiazepine in 100 ml. of methanol is added 2.24 g. (0.01 mole) of 5-(diethylamino)-2-oxo-valeric acid, hydrochloride [prepared by the method of Libman and Kutznetsov J. Gen. Chem. (USSR), 33, 1938 (1963)]. The mixture is kept under nitrogen at ambient temperature for 2 hours and then concentrated in vacuo. The residue is mixed with aqueous sodium bicarbonate and extracted with methylene chloride. The extract was washed with brine, dried over anhydrous magnesium sulfate and concentrated in vacuo. The residue of 7-chloro-2-[[1-carboxy-4-(diethylamino)-butylidene]hydrazino]-5-phenyl-3H-1,4-benzodiazepine is used without further purification.

EXAMPLE 14

7-Chloro-2-[[1-(methoxycarbonyl)-4-(diethylamino)-butylidene]hydrazino]-5-phenyl-3H-1,4-benzodiazepine A solution of 7-chloro-2-[[1-carboxy-4-(diethylamino)butylidene]hydrazino]-5-phenyl-3H-1,4-benzodiazepine in $CH_2Cl_2$ (10 ml.) is treated with stirring under $N_2$, with an ethereal solution of diazomethane (5 ml., 0.3 M). After ½ hour the solution is concentrated in vacuo giving 7-chloro-2-[[1-(methoxycarbonyl)-4-(diethylamino)-butylidene]hydrazino]-5-phenyl-3H-1,4-benzodiazepine as an oil, the nmr of which confirmed the structure. Nmr $(CDCl_3)$ δ 0.95 (t, 3, $CH_2CH_3$) 1.82 (m, 2, $CH_2CH_2CH_2$); 2.50 (m, 6, $CH_2CH_3$ and $CH_2CH_2N$), 2.27 (m, z, $CCH_2CH_2$), 3.77 (s, 3, $OCH_3$), 4.50 (broad s, z, 3—$CH_2$), between 6.80 and 7.85 (m, 8, arom H's).

EXAMPLE 15

9-Chloro-2-[3-(diethylamino)propyl]-7-phenyl-as-triazino[4,3-a][1,4]benzodiazepin-1(5H)-one The crude 7-chloro-2-[[1-(methoxycarbonyl)-4-(diethylamino)butylidene]hydrazino]-5-phenyl-3H-1,4-benzodiazepine of example 14 in glacial acetic acid (5 ml.) is stirred, under nitrogen, under reflux for 2 hours. The solution is mixed with ice water, neutralized with sodium bicarbonate and extracted with methylenechloride. The extract is washed with water, saturated sodium chloride solution, dried $(Na_2SO_4)$. Concentration in vacuo gives 9-chloro-2-[3-(diethylamino)propyl]-7-phenyl-as-triazino[4,3-a][1,4]benzodiazepin-1(5H)-one as an oil.

Nmr $(CDCl_3)$ δ 0.85 (t, 3, $CH_2CH_3$), between 1.65 and 3.15 (m, 10, $CH_2$), ab centered at 4.1 and 5.2 (2, J=−11Hz, 5—$CH_2$), between 7.0 and 7.95 (m, 8, arom H's).

Anal. calcd. for $C_{24}H_{26}ClN_5O$: C, 66.12; H, 6.01; Cl, 8.13; N, 16.07. Found: C, 64.95; H, 6.05; Cl, 8.53; N, 15.46.

EXAMPLE 16

7-Chloro-2-[(1-carboxymethylene)hydrazino]-5-phenyl-3H-1,4-benzodiazepine, methanol solvate To a stirred solution of 5.41 g. (0.019 mole) of 7-chloro-2-hydrazino-5-phenyl-3H-1,4-benzodiazepine in 100 ml. of methanol is added 3.09 g. (0.004 mole) of glyoxylic acid, hydrate, under nitrogen at ambient temperature, after one hour, the precipitate is collected, washed first with cold methanol and then ether, dried in a vacuum oven at 40° C. overnight to give 5.16 g. of 7-chloro-2-[(1-carboxymethylene)hydrazino]-5-phenyl-3H-1,4-benzodiazepine, methanol solvate, m.p. 164°–166° C. (dec). Concentration of the filtrate yields an additional 0.05 g. The ir, uv and nmr support the structure.

Anal. calcd. for $C_{17}H_{13}ClN_4O_2$: C, 59.92; H, 3.84; Cl, 10.41; N, 16.44. Found: C, 57.41; H, 4.81; cl, 9.43; N, 14.80; $CH_3OH$, 11.90.

Recalculation values corrected for melt solvate data: C, 60.10; H, 3.76; Cl, 10.70; N, 16.80.

EXAMPLE 17

7-Chloro-2-[[1-(methoxycarbonyl)methylene]-hydrazino]-5-phenyl-3H-1,4-benzodiazepine To a stirred suspension of 6.29 g. (0.017 mole) 7-chloro-2-[[1-carboxymethylene)hydrazino]-5-phenyl-3H-1,4-benzodiazepine, methanol solvate, in 300 ml. of methylene chloride is slowly added an ethereal solution of diazomethane (9.27 ml., 0.22 mole) under nitrogen, at ambient temperature. After an hour, the solvent is removed in vacuo and the residue is recrystallized from ethyl acetate to give 3.20 g. of 7-chloro-2-[[1-(methoxycarbonyl)methylene]hydrazino]-5-phenyl-3H-1,4benzodizepine. The analytical sample is recrystalized from ethyl acetate-hexane.

Anal. calcd. for $C_{18}H_{15}ClN_4O_2$: C, 60.93; H, 4.26; Cl, 9.99; N, 15.79. Found: C, 60.75; H, 4.52; Cl, 10.21; N, 15.45.

EXAMPLE 18

9-Chloro-7-phenyl-as-triazino[4,3-a][1,4]-benzodiazepin-1(5H)-one

A solution of 0.35 g. (0.001 mole) of 7-chloro-2-[[1-(methoxycarbonyl)methylene]hydrazino]-5-phenyl-3H-1,4-benzodiazepine in 10 ml. of 1,2,4-trichlorobenzene, under $N_2$, was heated at 200° for 5 hours. After cooling the solvent was evaporated in vacuo and the residue was chromatographed on silica gel. The product was eluted with chloroform in 15 ml. fractions. Fractions 12–19 were combined, evaporated, and the residue crystallized from ethyl acetate-hexane to yield 0.01 g. of 9-chloro-7-phenyl-as-triazino[4,3-a][1,4]benzodiazepin-1(5H)-one having m.p. 190°–194° C.

EXAMPLE 19

9-Chloro-7-phenyl-as-triazino[4,3-a][1,4]-benzodiazepin-1(5H)-one

7-Chloro-2-[(1-carboxymethylene)hydrazino]-5-phenyl-3H-1,4-benzodiazepine, methanol solvate, 1.71 g., 0.005 mole was dissolved in tetrahydrofuran and evaporated in vacuo. This was repeated twice more to remove the methanol. The residue was dissolved in tetrahydrofuran, under nitrogen, and 0.81 g. (0.005 mole) of 1,1'-carbonyldiimidazole was added. After stirring at room temperature for 1 hour and at reflux for 2 hours the solution was evaporated in vacuo, mixed with water and extracted with methylene chloride. After washing with water, drying over anhydrous sodium sulfate and evaporating in vacuo the residue was chromatographed on silica gel. The product was eluted with chloroform, evaporated, crystallized from ethyl acetate-hexane, yielding 0.33 g. of 9-chloro-7-phenyl-as-triazino[4,3-a][1,4]benzodiazepin-1(5H)-one having m.p. 191°–195° C.

Anal. calcd. for $C_{17}H_{11}ClN_4O$: C, 63.26; H, 3.44; Cl, 10.99; N, 17.36. Found: C, 63.00; H, 3.61; Cl, 10.68; N, 17.40.

EXAMPLE 20

9-Chloro-2-(dimethylaminomethyl)-7-phenyl-as-traizino[4,3-a][1,4]benzodiazepin-1(5H)-one A solution of 0.68 g. (0.002 mole) of 9-chloro-2-methyl-7-phenyl-as-triazino[4,3-a][1,4]benzodiazepin-1(5H)-one and 0.71 g. (0.004 mole) of N-bromosuccinimide in 20 ml. of carbon tetrachloride under nitrogen was stirred under reflux for 2 hours. The solid was dissolved by addition of methylene chloride and the solution was washed with 5% aqueous sodium bicarbonate and dried over sodium sulfate. After filtration and evaporation of the solvent the dark residue was dissolved in ethyl acetate, treated with decolorizing charcoal and chromatographed twice on silica gel, eluting with chlorofrom (15 ml. portions). Fractions 45–49 were found by nmr to contain predominately 9-chloro-2-(bromomethyl)-7-phenyl-as-triazino[4,3-a][1,4]benzodiazepin-1(5H)-one. Nmr (CDCl$_3$) δ 4.57 (s, CH$_2$Br), ab centered at 4.08 and 5.25 (J = −12Hz, 5—CH$_2$), between 7.1 and 8.0 (arom H's).

Others runs were made using bromide in place of N-bromosuccinimide and dimethylformamide as the solvent.

Crude 9-chloro-2-(bromomethyl)-7-phenyl-as-triazino[4,3-a][1,4]benzodiazepin-1(5H)-one, prepared as above, in dimethylformamide was mixed with an excess of methanolic dimethylamine. The purple solution was mixed with aqeuous sodium bicarbonate. The resulting solid was collected, washed with water and dissolved in methylene chloride. This solution was washed with aqueous sodium chloride, dried over sodium sulfate and evaporated to dryness. The dark residue was chromatographed on silica gel and eluted with 5% methanol in chloroform. Fractions 21–22 contained the desired 9 -chloro-2-(dimethylaminomethyl)-7-phenyl-as-triazino-[4,3-a][1,4]benzodiazepin-1(5H)-one. Nmr (CDCl$_3$) δ 2.40 (s, N(CH$_3$)$_2$), 3.65 (s, CH$_2$N), ab centered at 4.08 and 5.25 (J = −12Hz, 5—CH$_2$), between 7.2 and 7.9 (arom H's).

EXAMPLE 21

7-Chloro-2-[(1-carboxypropylidene)hydrazino]-5-phenyl-3H-1,4-benzodiazepine

In the manner given in Example 3, 7-chloro-2-hydrazino-5-phenyl-3H-1,4-benzodiazepine was stirred with α-oxobutyric acid at room temperature to give 7-chloro-2-[(1-carboxypropylidene)hydrazino]-5-phenyl-3H-1,4-benzodiazepine.

EXAMPLE 22

9-Chloro-2-ethyl-7-phenyl-as-triazino[4,3-a]-[1,4]benzodiazepin-1(5H)-one

To a solution of 1.84 g. (0.005 mole) of 7-chloro-2-[(1-carboxypropylidene)hydrazino]-5-phenyl-3H-1,4-benzodiazepine in 50 ml. of tetrahydrofuran under nitrogen, at 0° was added 0.9 g. (0.0055 mole) of 1,1'-carbonyldiimidazole. After stirring for 15 minutes at 0°, 1 hour at room temperature and 2 hours at reflux the solution was evaporated in vacuo. The residue was mixed with water and extracted with CH$_2$Cl$_2$. The extract was washed with water, and dried over Na$_2$SO$_4$. After concentration in vacuo the product was chromatographed on silica gel and eluted with 15 ml. portions of 1% MeOH—CHCl$_3$. Fractions 14–22 were combined and evaporated in vacuo giving 0.5 g. of 9-chloro-2-ethyl-7-phenyl-as-traizino[4,3-a]-[1,4]benzodiazepine-1(5H)-one as an oil. Nmr (CDCl$_3$) δ 1.29 (t, 3, CH$_2$CH$_3$), 2.90 (q, 2, CH$_2$CH$_3$), ab centered at 4.10 and 5.20 (2, J = −12Hz, 5CH$_2$), between 7.25 and 8.0 (m's 9, arometer.).

EXAMPLE 23

7-Chloro-2-[[1-(methoxycarbonyl)propylidene]hydrazino]-5-phenyl-3H-1,4-benzodiazepine In the manner given in Example 10, 7-chloro-2-[(1-carboxypropylidene)hydrazino]-5-phenyl-3H-1,4-benzodiazepine is treated with etheral diazomethane to give 7-chloro-2-[[1-(methoxycarbonyl)propylidene]-hydrazino]-5-phenyl-3H-1,4-benzodiazepine.

EXAMPLE 24

9-Chloro-2-ethyl-7-phenyl-as-triazino-[4,3-a][1,4]benzodiazepin-1(5H)-one

In the manner given in Example 6, a solution of 7-chloro-2-[[1-(methoxycarbonyl)propylidene]hydrazino]-5-phenyl-3H-1,4-benzodiazepine is heated to reflux in acetic acid to give 9-chloro-2-ethyl-7-phenyl-as-triazino[4,3-a][1,4]benzodiazepin-1(5H)-one, having an nmr spectrum the same as that of Example 22.

EXAMPLE 25

7-Chloro-2-[[1,2-bis(ethoxycarbonyl)ethylidene]hydrazino]-5-phenyl-3H-1,4-benzodiazepine An aqueous solution of 1.26 g. (0.006 mole) of diethyl oxalacetate sodium salt was acidified with hydrochloric acid and extracted with methylene chloride. The extract was dried over sodium sulfate and evaporated to dryness in vacuo. The resulting oil in 30 ml. of methanol under N$_2$ was mixed with 0.812 g. (0.003 mole) of 7-chloro-2-hydrazino-5-phenyl-3H-1,4-benzodiazepine and allowed to stand at room temperature for 1.5 hours. The solution was evaporated in vacuo, dissolved in methylene chloride, washed with dilute sodium hydroxide and dried over magnesium sulfate. After filtration the solution was evaporated in vacuo giving 7-chloro-2-[[1,2-bis-(ethoxycarbonyl)ethylidene]hydrazino]-5-phenyl-3H-1,4-benzodiazepine as an oil. Nmr confirmed the structure. Nmr (CDCl$_3$) δ 1.20 and 1.22 (2 t's, 6, CH$_2$CH$_3$), 4.13 (q, 6, CH$_2$CH$_3$), 4.48 (broad s, 2, 3—CH$_2$), between 6.93 and 7.83 (m's, 8, arom H's).

EXAMPLE 26

2-(Carboethoxymethyl)-9-chloro-7-phenyl-as-triazino[4,3-a][1,4]benzodiazepin-1(5H)-one (tautomeric form)

The crude 7-chloro-2-[[1,2-bis (ethoxycarbonyl)-ethylidene]hydrazino]-5-phenyl-3H-1,4-benzodiazepine of Example 23 was dissolved in 10 ml. of acetic acid and stirred under reflux, under N$_2$ for 1.5 hours. The solution was evaporated in vacuo, neutralized with dilute sodium bicarbonate, and extracted with methylene chloride. The extract was washed with water, saturated sodium chloride solution, dried over sodium sulfate, and evaporated in vacuo. The residue was taken up in ethyl acetate, treated with decolorizing charcoal, concentrated, and diluted with hexane. The resulting solid was recrystallized from ethyl acetate-hexane giving 0.15 g. of 2-carbethoxymethyl-9-chloro-7-phenyl-as-triazine[4,3-a][1,4]benzodiazepine-1(5H)-one as the tautomeric 2-(carbethoxymethylene)-9-chloro-2,5-dihydro-7-phenyl-as-triazino[4,3-a][1,4]benzodiazepin-1-one. This structure was confirmed by ir, mass spec [M+408 (1Cl)] and nmr (CDCl$_3$) δ 1.25 (t, 3, CH$_2$CH$_3$), 4.20 (q, 2, CH$_2$CH$_3$), ab centered at $_0$4.05 and 4.82 (2, J= −12 Hz, 5—CH$_2$), 5.58 (s, 1, =CHC—), between 7.25 and 7.83 (m's, 8, arom H's).

Anal. calcd. for C$_{21}$H$_{17}$Cl$_1$N$_4$O$_3$: C, 61.69; H, 4.19; Cl, 8.67; N, 13.70; Found: C, 61.36; H, 4.28; Cl, 8.59; N, 13.77.

EXAMPLE 27

7-Chloro-2-[(1,3-biscarboxypropylidene)-hydrazino]-5-phenyl-3H-1,4-benzodiazepine To a mixture of 2.86 g. (0.01 mole) of 7-chloro-2-hydrazino-5-phenyl-3H-1,4-benzodiazepine in 70 ml. methanol was added 2.92 g. (0.02 mole) of α-ketoglutaric acid in 30 ml. of methanol. After stirring for 1.5 hours at room temperature the mixture was cooled to 3° C. and filtered to give 3.88 g. (94.6%) of 7-chloro-2-[(1,3-biscarboxypropylidene)hydrazino]-5-phenyl-3H-1,4-benzodiazepine.

Anal. calcd. for C$_{20}$H$_{17}$ClN$_4$O$_4$: C, 58.18; H, 4.15; Cl, 8.59; N, 13.57. Found: C, 57.65; H, 4.34; Cl, 8.45; N, 13.25.

EXAMPLE 28

7-Chloro-2-[[1,3-bis(methoxycarbonyl)-propylidene]-hydrazino]-5-phenyl-3H-1,4-benzodiazepine To a cold solution of 2.06 g. (0.005 mole) of 7-chloro-2-[(1,3-bis-carboxypropylidene)hydrazino]-5-phenyl-3H-1,4-benzodiazepine in 150 ml. of methylene chloride was added, under nitrogen, with stirring, 65 ml. (0.011 mole) of an ethereal solution of diazomethane. After stirring at 0° C. for 1 hour 1 ml. of acetic acid was added and the solution was washed with saturated aqueous sodium bicarbonate, then with water, and dried over Na$_2$SO$_4$. After filtration the CH$_2$Cl$_2$ solution was evaporated to dryness in vacuo giving 7-chloro-2-[[1,3-bis(methoxycarbonyl)propylidene]-hydrazino]-5-phenyl-3H-1,4-benzodiazepine as an oil. Tlc (SiO$_2$, 10% MeOH/CHCl$_3$) showed one spot R$_f$ 8.5; and nmr confirmed the structure. Nmr (CDCl$_3$) δ between 2.48 and 3.33 (m, 4, CH$_2$CH$_2$), 3.66 (s, 3, CH$_3$), 3.84 (s, 3, CH$_3$), 4.54 (s, 2, 3—CH$_2$), between 7.00 and 7.82 (m's, 8, arom H's).

EXAMPLE 29

2-[2-(Carbomethoxy)ethyl]-9-chloro-7-phenyl-as-triazino[4,3-a][1,4]benzodiazepine-1(5H)-one The crude 7-chloro-2-[[1,3-bis(methoxycarbonyl)-propylidene]hydrazino]-5-phenyl-3H-1,4-benzodiazepin of Example 28 was dissolved in 50 ml. of acetic acid, under N$_2$, and stirred under reflux for 1 hour. After cooling the reaction mixture was mixed with ice water, neutralized with sodium bicarbonate, and extracted with methylene chloride. After washing the extract with water, saturated sodium chloride solution, and drying over Na$_2$SO$_4$, the solution was filtered and evaporated to dryness in vacuo. The product was crystallized from ethyl acetate-hexane yielding 5.8 g. of 2-[2-(carbomethoxy)ethyl]-9-chloro-as-triazino[4,3-a][1,4]benzodiazepin-1(5H)-one, m.p. 145°–148° C. Additional product (1.45 g.) was obtained from the filtrate. Ir and nmr confirms the structure.

Anal. calcd. for C$_{21}$H$_{17}$ClN$_4$O$_3$: C, 61.69; H, 4.19; Cl, 8.67; N, 13.70; Found: C, 61.86; H, 4.45; Cl, 8.69; N, 13.53.

EXAMPLE 30

7-Chloro-2-[[1,3-bis[(p-nitrophenoxy)carbonyl]-propylidene]hydrazino]-5-phenyl-3H-1,4-benzodiazepine A solution of 7-chloro-2-[(1,3-biscarboxypropylidene)-hydrazino]-5-phenyl-3H-1,4-benzodiazepine in tetrahydrofuran can be converted to the disodium salt with sodium hydride or to the potassium salt with potassium t-butoxide. To this can be added a solution of p-fluoronitrobenzene and the mixture stirred at 0°–100°. The ester can be isolated by filtering off the sodium (or potassium) fluoride and evaporating the solution or by dissolving the sodium (or potassium fluoride in cold water and extracting the ester with methylene chloride, followed by drying and evaporating the extract to give 7-chloro-2-[[1,3-bis[(p-nitrophenoxy)carbonyl]propylidene]hydrazino]-5-phenyl-3H-1,4-benzodiazepine.

EXAMPLE 31

9-Chloro-2-[2-[(p-nirophenoxy)carbonyl]-ethyl]-7-phenyl-as-triazino[4,3-a][1,4]benzodiazepine-1(5H)-one In the manner given in Example 29, a solution of 7-chloro-2-[[1,3-bis[(p-nitrophenoxy)carbonyl]-propylidene]hydrazino]-5-phenyl-3H-1,4-benzodiazepine in acetic acid can be warmed at 25°–100° C. to give 9-chloro-2-[2-[(p-nitrophenoxy)carbonyl]ethyl]-7-phenyl-as-triazino-[4,3-a][1,4]benzodiazepin-1(5H)-one.

EXAMPLE 32

2-Aminoethyl-9-chloro-7-phenyl-as-triazino-[4,3-a][1,4]benzodiazepin-1(5H)-one

A solution of 9-chloro-2-[2-[(p-nitrophenoxy)carbonyl]-ethyl]-7-phenyl-as-triazino[4,3-a][1,4]benzodiazepin-1(5H)-one in tetrahydrofuran can be treated with sodium azide to give 9-chloro-2-[2-(azidocarbonyl)ethyl)]-7-phenyl-as-triazino[4,3-a][1,4]benzodiazepin-1(5H)-one. Without purification this can be heated at 20°–150° C. and rearranged under the conditions of the Curtius Reaction (P. A. S. Smith, "Organic Reactions", Vol. III, John Wiley and Sons, New York, N.Y. 1946 pages 337–449) to give 9-chloro-2-[2-(isocyanato)ethyl)]-7-phenyl-as-triazino[4,3-a][1,4]-benzodiazepin-1(5H)-one. This can be hydrolyzed by Curtius Reaction Conditions (Smith loc. cit) to give 2-(aminoethyl)-9-chloro-7-phenyl-as-triazino[4,3-a][1,4]-benzodiazepin-1(5H)-one.

EXAMPLE 33

9-Chloro-7-phenyl-2-(pyrrolidinoethyl)-as-triazino]4,3-a][1,4]benzodiazepin-1(5H)-one A solution of 9-chloro-2-(aminoethyl)-7-phenyl-as-triazino[4,3-a][1,4benzodiazepin-1(5H)-one, with 1 molar equivalent of 1,4-dibromobutane and 2 molar equivalents of a tertiary amine (for example N,N-diisopropylethylamine) can be allowed to stand at room temperature or heated at reflux to give 9-chloro-7-phenyl-2-(pyrrolidylethyl)-as-triazino[4,3-a][1,4-benzodiazepine-1(5H)-one.

EXAMPLE 34

7-Bromo-2-[[1-(methoxycarbonyl)ethylidene]-hydrazino]-5-(2-pyridyl)-3H-1,4-benzodiazepine In the manner given in Example 1, 7-bromo-2-hydrazino-5-(2-pyridyl)-3H-1,4-benzodiazepine can be stirred with methyl pyruvate at room temperature to give 7-bromo-2-[[1-(methoxycarbonyl)ethylidene]hydrazino]-5-(2-pyridyl)-3H-1,4-benzodiazepine.

EXAMPLE 35

9-Bromo-2-methyl-7-(2-pyridyl)-as-triazino-[4,3-a][1,4]benzodiazepin-1(5H)-one

In the manner given in Example 6, a solution of 7-bromo-2-[[1-(methoxycarbonyl)ethylidene]hydrazino]-5-(2-pyridyl)-3H-1,4-benzodiazepine can be heated to reflux with acetic acid to give 9-bromo-2-methyl-7-(2-pyridyl)-as-triazino[4,3-a][1,4]benzodiazepin-1(5H)-one.

EXAMPLE 36

7-Nitro-2-[[1-(methoxycarbonyl)ethylidene]-hydrazino]-5-(o-chloropheny)-3H-1,4-benzodiazepine In the manner given in Example 1, 7-nitro-2-hydrazino-5-(o-chlorophenyl)-3H-1,4-benzodiazepine can be stirred with methyl pyruvate at room temperature to give 7-nitro-2-[[1-(methoxycarbonyl)ethylidene]hydrazino]-5-(o-chlorophenyl)-3H-1,4-benzodiazepine.

EXAMPLE 37

9-Nitro-2-methyl-7-(o-chlorophenyl)-as-triazino[4,3-a][1,4]benzodiazepin-1(5H)-one In the manner given in Example 6, a solution of 2-7-nitro-2-[[1-(methoxycarbonyl)ethylidene]hydrazino]-5-(o-chlorophenyl)-3H-1,4-benzodiazepine can be heated to reflux with acetic acid to give 9-nitro-2-methyl-7-(o-chlorophenyl)-as-triazino[4,3-a][1,4]benzodiazepin-1(5H)-one.

EXAMPLE 38

7-Fluoro-2-[[1-(methoxycarbonyl)ethylidene]-hydrazino]-5-(o-chlorophenyl)-3H-1,4-benzodiazepine In the manner given in Example 1, 7-fluoro-2-hydrazino-5-(o-chlorophenyl)-3H-1,4-benzodiazepine can be stirred with methyl pyruvate at room temperature to give 7-fluoro-2-[[1-(methoxycarbonyl)ethylidene]hydrazino]-5-(o-chlorophenyl)-3H-1,4-benzodiazepine.

EXAMPLE 39

9-Fluoro-2-methyl-7-(o-chlorophenyl)-as-triazino[4,3-a][1,4]benzodiazepin-1(5H)-one In the manner given in Example 6, a solution of 2-7-fluoro-2-[[1-(methoxycarbonyl)ethylidene]hydrazino]-5-(o-chlorophenyl)-3H-1,4-benzodiazepine can be heated to reflux with acetic acid to give 9-fluoro-2-methyl-7-(o-chlorophenyl)-as-triazino[4,3-a][1,4]benzodiazepin-1(5H)-one.

EXAMPLE 40

7-(Trifluoromethyl)-2-[[1-(methoxycarbonyl)-ethylidene]hydrazino]-5-(o-chlorophenyl)-3H-1,4-benzodiazepine In the manner given in Example 1, 7-(trifluoromethyl)-2-hydrazino-5-(o-chlorophenyl)-3H-1,4-benzodiazepine can be stirred with methyl pyruvate at room temperature to give 7-(trifluoromethyl)-2-[[1-(methoxycarbonyl)ethylidene]hydrazino]-5-(o-chlorophenyl)-3H-1,4-benzodiazepine.

EXAMPLE 41

9-(Trifluoromethyl)-2-methyl-7-(o-chlorophenyl)-as-triazino[4,3-a][1,4]benzodiazepin-1(5H)-one In the manner given in Example 5, a solution of 7-(trifluoromethyl)-2-[[1-(methoxycarbonyl)ethylidene]-hydrazino]-5-(o-chlorophenyl)-3H-1,4-benzodiazepine can be heated to reflux with 1,2,4-trichlorobenzene to give 9-trifuloromethyl)-2-methyl-7-(o-chlorophenyl)-as-triazino[4,3-a][1,4]benzodiazepin-1(5H)-one.

EXAMPLE 42

5-(o-Chlorophenyl)-2-[[1-(methoxycarbonyl)-ethylidene]hydrazino]-3H-1,4-benzodiazepine In the manner given in Example 1, 2-hydrazino-5-(o-chlorophenyl)-3H-1,4-benzodiazepine can be stirred with methyl pyruvate at room temperature to give 5-(o-chlorophenyl)-2-[[1-(methoxycarbonyl)ethylidene]-hydrazino]-3H-1,4-benzodiazepine.

EXAMPLE 43

2-Methyl-7-(o-chlorophenyl)-as-triazino-[4,3-a]-[1,4]benzodiazepin-1(5H)-one

In the manner given in Example 5, a solution of 2-5-(o-chlorophenyl)-2-[[1-(methoxycarbonyl)ethylidene]-hydrazino]-3H-1,4-benzodiazepine can be heated to reflux with 1,2,4-trichlorobenzene to give 2-methyl-7-(o-chlorophenyl)-as-triazino-[4,3-a][1,4]benzodiazepin-1(5H)-one.

EXAMPLE 44

7-Bromo-2-[[1-(methoxycarbonyl)ethylidene]-hydrazino]-5-(o-chlorophenyl)-3H-1,4-benzodiazepine In the manner given in Example 1, 7-bromo-2-hydrazino-5-(o-chlorophenyl)-3H-1,4-benzodiazepine can be stirred with methyl pyruvate at room temperature to give 7-bromo-2-[[1-(methoxycarbonyl)ethylidene]hydrazino]-5-(o-chlorophenyl)-3H-1,4-benzodiazepine.

EXAMPLE 45

9-Bromo-2-methyl-7-(o-chlorophenyl)-as-triazino[4,3-a][1,4]benzodiazepin-1(5H)-one In the manner given in Example 6, a solution of 7-bromo-2-[[1-(methoxycarbonyl)ethylidene]hydrazino]-5-(o-chlorophenyl) -3H-1,4-benzodiazepine can be heated at reflux with acetic acid to give 9-chloro-2-methyl-7-(o-chlorophenyl)-as-triazino[4,3-a][1,4]benzodiazepine-1(5H)-one.

EXAMPLE 46

7-Chloro-2-[(1-carboxybutylidene)hydrazino]-5-(o-chlorophenyl)-3H-1,4-benzodiazepine In the manner given in Example 9, 7-chloro-2-hydrazino-5-(o-chlorophenyl)-3H-1,4-benzodiazepine can be stirred with α-oxopentanoic acid at room temperature to give 7-chloro-2-[(1-carboxybutylidene)hydrazino]-5-(o-chlorophenyl)-3H-1,4-benzodiazepine.

EXAMPLE 47

7-Chloro-2-[[1-(methoxycarbonyl)butylidene]hydrazino]-5-(o-chlorophenyl)-3H-1,4-benzodiazepine In the manner given in Example 10, a solution of 7-chloro-2-[(1-carboxybutylidene)hydrazino]-5-(o-chlorophenyl)-3H-1,4-benzodiazepine can be treated with ethereal diazomethane to give 7-chloro-2-[[1-(methoxycarbonyl)-butylidene]hydrazino]-5-(o-chlorophenyl)-3H-1,4-benzodiazepine.

EXAMPLE 48

9-Chloro-2-propyl-7-(o-chlorophenyl)-as-triazino[4,3-a][1,4]benzodiazepin-1(5H)-one In the manner given in Example 6, a solution of 7-chloro-2-[[1-methoxycarbonyl)butylidene]hydrazino]-5-(o-chlorophenyl)-3H-1,4-benzodiazepine can be heated to reflux with acetic acid to give 9-chloro-2-propyl-7-(o-chlorophenyl)-as-triazino[4,3-a][1,4]benzodiazepin-1(5H)-one.

EXAMPLE 49

7-Chloro-2-[(1-carboxy-3-butenylidene)-hydrazino]-5-(o-chlorophenyl)-3H-1,4-benzodiazepine In the manner given in Example 9, 7-chloro-2-hydrazino-5-(o-chlorophenyl)-3H-1,4-benzodiazepine can be stirred with 2-oxo-4-pentenoic acid at room temperature to give 7-chloro-2-[(1-carboxy-3-butenylidene)-hydrazino]-5-(o-chlorophenyl)-3H-1,4-benzodiazepine.

EXAMPLE 50

7-Chloro-2-[[1-(methoxycarbonyl)-3-butenylidene]-hydrazino]-5-(o-chlorophenyl)-3H-1,4-benzodiazepine In the manner given in Example 10, a solution of 7-chloro-2-[(1-carboxy-3-butenylidene)hydrazino]-5-(o-chlorophenyl)-3H-1,4-benzodiazepine can be treated with ethereal diazomethane to give 7-chloro-2-[[1-(methoxycarbonyl)-3-butenylidene]hydrazino]-5-(o-chlorphenyl)-3H-1,4-benzodiazepine.

EXAMPLE 51

9-Chloro-2-allyl-7-(o-chlorophenyl)-as-triazino[4,3-a][1,4]benzodiazepin-1(5H)-one In the manner given in Example 6, a solution of 7-chloro-2-[[1-(methoxycarbonyl)-3-butenylidene]hydrazino]-5-(o-chlorophenyl)-3H-1,4-benzodiazepine can be heated to reflux with acetic acid to give 9-chloro-2-allyl-7-(o-chlorophenyl)-as-triazino[4,3-a][1,4]benzodiazepin-1(5H)-one.

EXAMPLE 52

7-Chloro-2-[(1-carboxy-2-hydroxyethylidene)-hydrazino]-5-(o-chlorophenyl)-3H-1,4-benzodiazepine In the manner given in Example 9, 7-chloro-2-hydrazino-5-(o-chlorophenyl)-3H-1,4-benzodiazepine can be stirred with 3-hydroxy-2-oxopropionic acid at room temperature to give 7-chloro-2-[(1-carboxy-2-hydroxymethylidene)hydrazino]-5-(o-chlorophenyl)-3H-1,4-benzodiazepine.

EXAMPLE 53

7-Chloro-2-[[1-(methoxycarbonyl)-2-hydroxyethylidene]hydrazino]-5-(o-chlorophenyl)-3H-1,4-benzodiazepine In the manner given in Example 10, a solution of 7-chloro-2-[(1-carboxy-2-hydroxyethylidene)hydrazino]-5-(o-chlorophenyl)-3H-1,4-benzodiazepine can be treated with ethereal diazomethane to give 7-chloro-2-[[1-(methoxycarbonyl)-2-hydroxyethylidene]hydrazino]-5-(o-chlorophenyl)-3H-1,4-benzodiazepine.

EXAMPLE 54

9-Chloro-2-hydroxymethyl-7-(o-chlorophenyl)-as-triazino[4,3-a][1,4]benzodiazepin-1(5H)-one In the manner given in Example 5, a solution of 7-chloro-2-[[1-(methoxycarbonyl)-2-hydroxyethylidene]-hydrazino]-5-(o-chlorophenyl)-3H-1,4-benzodiazepine is heated to reflux with 1,2,4-trichlorobenzene to give 9-chloro-2-hydroxymethyl-7-(o-chlorophenyl)-as-triazino-[4,3-a][1,4]benzodiazepin-1(5H)-one.

EXAMPLE 55

7-Chloro-2-[[1-carboxy-4-(4-methylpiperazino)-butylidene]hydrazino]-3-methyl-5-phenyl-3H-1,4-benzodiazepine In the manner given in Example 13, 7-chloro-2-hydrazino-3-methyl-5-phenyl-3H-1,4-benzodiazepine can be stirred with 5-(4-methylpiperazino)-2-oxopentanoic acid at room temperature to give 7-chloro-2[[1-carboxy-4-(4-methylpiperazino)butylidene]hydrazino]-3-methyl-5-phenyl-3H-1,4-benzodiazepine.

EXAMPLE 56

7-Chloro-2-[[1-(methoxycarbonyl)-4-(4-methylpiperazino)butylidene]hydrazino]-3-methyl-5-phenyl-3H-1,4-benzodiazepine In the manner given in Example 14, a solution of 7-chloro-2-[[1-carboxy-4-(4-methylpiperazino)-butylidene]-hydrazino]-3-methyl-5-phenyl-3H-1,4-benzodiazepine can be treated with ethereal diazomethane to give 7-chloro-2-[[1-(methoxycarbonyl)-4-(4-methylpiperazino)butylidene]-hydrazino]-3-methyl-5-phenyl-3H-1,4-benzodiazepine.

EXAMPLE 57

9-Chloro-5-methyl-2-[3-(4-methylpiperazino)-propyl]-7-phenyl-as-traizino[4,3-a][1,4]benzodiazepin-1(5H)-one.

In the manner given in Example 15, a solution of 7-chloro-2-[[1-(methoxycarbonyl)-4-(4-methylpiperazino)-butylidene]hydrazino]-3-methyl-5-phenyl- 3H-1,4-benzodiazepine in acetic acid can be heated to reflux to give 9-chloro-5-methyl-2-[3-(4-methylpiperazino)propyl]-7-phenyl-as-triazino[4,3-a][1,4]benzodiazepin-1(5H)-one.

EXAMPLE 58

7-Chloro-2-[[1-carboxy-3-[4-hydroxyethyl)-piperazino]propylidene]hydrazino]-5-phenyl-3H-1,4-benzodiazepine In the manner given in Example 13, 7-chloro-2-hydrazino-5-phenyl-3H-1,4-benzodiazepine can be reacted with 4-(4-(2-hydroxyethyl)piperazino]-2-oxobutonic acid to give 7-chloro-2-[[1-carboxy-3-[4-(2-hydroxyethyl)-piperazino]propylidene]hydrazino]-5-phenyl-3H-1,4-benzodiazepine.

EXAMPLE 59

7-Chloro-2-[[1-(methoxycarbonyl)-3-[4-(2-hydroxyethyl)piperazino]propylidene]hydrazino]-5-phenyl-3H-1,4-benzodiazepine In the manner given in Example 14, 7-chloro-2-[[1-carboxy-3-[4-(2-hydroxyethyl)piperazino]-propylidene]hydrazino]-5-phenyl-3H-1,4-benzodiazepine can be treated with ethereal diazomethane to give 7-chloro-2-[[1-(methoxycarbonyl)-3-[4-(2-hydroxyethyl)piperazino]-propylidene]hydrazino]-5-phenyl-3H-1,4-benzodiazepine.

EXAMPLE 60

9-Chloro-2-[2-[4-(2-hydroxyethyl)piperazino]-ethyl]-7-phenyl-as-triazino[4,3-a][1,4]benzodiazepin-1(5H)-one.

In the manner given in Example 15, a solution of 7-chloro-2-[[1-(methoxycarbonyl)-3-[4-(2-hydroxyethyl)-piperazino]propylidene]hydrazino]-5-phenyl-3H-1,4-benzodiazepine in acetic acid can be heated to reflux to give 9-chloro-2-[2-[4-(2-hydroxyethyl)-piperazino]ethyl]-7-phenyl-as-triazino[4,3-a][1,4]benzodiazepin-1(5H)-one.

EXAMPLE 61

7-Chloro-2-[(1-carboxy-4-morpholinobutylidene)hydrazino]-5-phenyl-3H-1,4-benzodiazepine In the manner given in Example 13, 7-chloro-2-hydrazino-5-phenyl-3H-1,4-benzodiazepine can be stirred with 5-morpholino-2-oxopentanoic acid to give 7-chloro-2-[(1-carboxy-4-morpholinobutylidene)hydrazino]-5-phenyl-3H-1,4-benzodiazepine.

EXAMPLE 62

7-Chloro-2-[[1-(methoxycarbonyl)-4-morpholinobutylidene]hydrazino]-5-phenyl-3H-1,4-benzodiazepine In the manner given in Example 14, 7-chloro-2-[(1-carboxy-4-morpholinobutylidene)hydrazino]-5-phenyl-3H-1,4-benzodiazepine can be treated with ethereal diazomethane to give 7-chloro-2-[[1-(methoxycarbonyl)-4-morpholinobutylidene]hydrazino]-5-phenyl-3H-1,4-benzodiazepine.

EXAMPLE 63

9-Chloro-2-(3-morpholinopropyl)-7-phenyl-as-triazino[4,3-a][1,4]benzodiazepin-1(5H)-one In the manner given in Example 15, a solution of 7-chloro-2-[[1-(methoxycarbonyl)-4-morpholinobutylidene]-hydrazino]-5-phenyl-3H-1,4-benzodiazepine, in acetic acid, can be heated to reflux to give 9-chloro-2-(3-morpholinopropyl)-7-phenyl-as-triazino[4,3-a][1,4]benzodiazepin-1(5H)-one.

EXAMPLE 64

7-Chloro-2-[[1-carboxy-4-(diethylamino)-butylidene]-hydrazino]-5-(o-chlorophenyl)-3H-1,4-benzodiazepine can be stirred with 5-(diethylamino)-2-oxopentanoic acid at room temperature to give 7-chloro-2-[[1-carboxy-4-(diethylamino)butylidene]-hydrazino]-5-(o-chlorophenyl)-3H-1,4-benzodiazepine.

EXAMPLE 65

7-Chloro-2-[[1-(methoxycarbonyl)-4-(diethylamino)-butylidene]hydrazino]-5-(o-chlorophenyl)-3H-1,4-benzodiazepine In the manner given in Example 14, 7-chloro-2-[[1-carboxy-4-(diethylamino)butylidene]hydrazino]-5-(o-chlorophenyl)-3H-1,4-benzodiazepine can be treated with ethereal diazomethane to give 7-chloro-2-[[1-(methoxycarbonyl)-4-(diethylamino)butylidene]hydrazino]-5-(o-chlorophenyl)-3H-1,4-benzodiazepine.

EXAMPLE 66

9-Chloro-2-[3-(diethylamino)propyl]-7-(o-chlorophenyl)-as-traizino[4,3-a][1,4]benzodiazepin-1(5H)-one.

in the manner given in Example 15, a solution of 7-chloro-2-[[1-methoxycarbonyl)-4-(diethylamino)-butylidene]hydrazino]-5-(o-chlorophenyl)-3H-1,4-benzodiazepine in acetic acid can be heated to reflux to give 9-chloro-2-[3-(diethylamino)propyl]-7-(o-chlorophenyl)-as-triazino[4,3-a][1,4]benzodiazepin-1(5H)-one.

EXAMPLE 67

7-Chloro-2-[(1-carboxy-2-pyrrolidinoethylidene)hydrazino]-5-phenyl-3H-1,4-benzodizepine In the manner given in Example 13, 7-chloro-2-hydrazino-5-phenyl-3H-1,4-benzodiazepine can be stirred with 2-oxo-3-pyrrolidinopropionic acid at room temperature to give 7-chloro-2-[(1-carboxy-2-pyrrolidinoethylidene)-hydrazino]-5-phenyl-3H-1,4-benzodiazepine.

EXAMPLE 68

7-Chloro-2-[[1-(methoxycarbonyl)-2-pyrrolidinoethyliden]hydrazino]-5-phenyl-3H-1,4-benzodiazepine In the manner given in Example 14, 7-chloro-2-[(1-carboxy-2-pyrrolidinoethylidene)hydrazino]-5-phenyl-3H-1,4-benzodiazepine can be treated with ethereal diazomethane to give 7-chloro-2-[[1-(methoxycarbonyl)-2-pyrrolidinoethylidene]hydrazino]-5-phenyl-3H-1,4-benzodiazepine.

EXAMPLE 69

9-Chloro-2-pyrrolidinomethyl-7-phenyl-as-triazino[4,3-a][1,4]benzodiazepin-1(5H)-one.

In the manner given in Example 15, a solution 7-chloro-2-[[1-(methoxycarbonyl)-2-pyrrolidnoethylidene]hydrazino]-5-phenyl-3H-1,4-benzodiazepine can be heated to reflux with acetic acid to give 9- chloro-2-pyrrolidinomethyl-7-phenyl-as-traizino[4,3-a][1,4]-benzodiazepin-1(5H)-one.

EXAMPLE 70

7-Nitro-2-[(1-carboxy-4-piperidinobutylidene)-hydrazino]-5-phenyl-3H-1,4-benzodiazepine In the manner given in Example 13, 7-nitro-2-hydrazino-5-phenyl-3H-1,4-benzodiazepine can be stirred with 2-oxo-5-piperidinopentanoic acid at room temperature to give 7-nitro-2-[(1-carboxy-4-piperidinobutylidene)-hydrazino]-5-phenyl-3H-1,4-benzodiazepine.

EXAMPLE 71

7-Nitro-2-[[1-(methoxycarbonyl)-4-piperidinobutylidene]hydrazino]-5-phenyl-3H-1,4-benzodiazepine In the manner given in Example 14, 7-nitro-2-[(1-carboxy-4-piperidinobutylidene)hydrazino]-5-phenyl-3H-1,4-benzodiazepine can be treated with ethereal diazomethane to give 7-nitro-2[[1-(methoxycarbonyl)-4-piperidinobutylidene]hydrazino]-5-phenyl-3H-1,4-benzodiazepine.

EXAMPLE 72

9-Nitro-2-(3-piperidinopropyl)-7-phenyl-as-triazino[4,3-a][1,4]benzodiazepin-1(5H)-one.

In the manner given in Example 15, a solution of 7-nitro-2-[[1-(methoxycarbonyl)-4-piperidinobutylidene]-hydrazino]-5-phenyl-3H-1,4-benzodiazepine in acetic acid can be heated to reflux to give 9-nitro-2-(3-piperidinopropyl)-7-phenyl-as-triazino[4,3-a][1,4]benzodiazepin-1(5H)-one.

EXAMPLE 73

7-Bromo-2-[(1-carboxy-3-methoxypropylidene)-hydrazino]-5-(o-chlorophenyl)-3H-1,4-benzodiazepine.

In the manner given in Example 9, 7-bromo-2-hydrazino-5-(o-chlorophenyl)-3H-1,4-benzodiazepine can be stirred with 4-methoxy-2-oxobutyric acid at room temperature to give 7-bromo-2-[(1-carboxy-3-methoxypropylidene)-hydrazino]-5-(o-chlorophenyl)-3H-1,4-benzodiazepine.

EXAMPLE 74

7-Bromo-2-[[1-(methoxycarbonyl)-3-methoxypropylidene]hydrazino]-5-(o-chlorophenyl)-3H-1,4-benzodiazepine.

In the manner given in Example 10, 7-bromo-2-[(1-carboxy-3-methoxypropylidene)hydrazino]-5-(o-chlorophenyl)-3H-1,4-benzodiazepine can be treated with ethereal diazomethane to give 7-bromo-2-[[1-(methoxycarbonyl)-3-methoxypropylidene]hydrazino]-5-(o-chlorophenyl)-3H-1,4-benzodiazepine.

EXAMPLE 75

9-Bromo-2-(2-methoxyethyl)-7-(o-chlorophenyl)-as-triazino[4,3-a][1,4]benzodiazepin-1(5H)-one In the manner given in Example 6, a solution of 7-bromo-2-[[1-(methoxycarbonyl)-3-methoxypropylidene]-hydrazino]-5-(o-chlorophenyl)-3H-1,4-benzodiazepine in acetic acid can be heated to reflux to give 9-bromo-2-(2-methoxyethyl)-7-(o-chlorophenyl)-as-triazino[4,3-a]-[1,4]benzodiazepin-1(5H)-one.

EXAMPLE 76

7-(Trifluoromethyl)-2-[[1-carboxy-3-(dipropylamino)propylidene]hydrazino]-5-(o-fluorophenyl)-3H-1,4-benzodiazepine.

In the manner given in Example 13, 7-(trifluoromethyl)-2-hydrazino-5-(o-fluorophenyl)-3H-1,4-benzodiazepine can be stirred with 2-oxo-4-(dipropylamino)-butyric acid at room temperature to give 7-(trifluoromethyl)-2-[[1-carboxy-3-(dipropylamino)-propylidene]-hydrazino]-5-(o-fluorophenyl)-3H-1,4-benzodiazepine.

EXAMPLE 77

7-(Trifluoromethyl)-2-[[1-(methoxycarbonyl)-3-(dipropylamino)propylidene]hydrazino]-5-(o-fluorophenyl)-3H-1,4-benzodiazepine.

In the manner given in Example 14, 7-(trifluoromethyl)-2-[[1-carboxy-3-(dipropylamino)propylidene]-hydrazino]-5-(o-fluorophenyl)-3H-1,4-benzodiazepine can be treated with ethereal diazomethane to give 7-(trifluoromethyl)-2-[[1-(methoxycarbonyl)-3-(dipropylamino)propylidene]hydrazino]-5-(o-fluorophenyl)-3H-1,4-benzodiazepine.

EXAMPLE 78

9-(Trifluoromethyl)-2-[2-(dipropylaminomethyl]-7-(o-fluorophenyl)-as-triazino[4,3-a][1,4]-benzodiazepine-1(5H)-one.

In the manner given in Example 15, a solution of 7-(trifluoromethyl)-2-[[1-(methoxycarbonyl)-3-(dipropylamino)propylidene]hydrazino]-5-(o-fluorophenyl)-3H-1,4-benzodiazepine in acetic acid can be heated to reflux to give 9-(trifluoromethyl)-2-[2-(dipropylamino)ethyl]-7-(o-fluorophenyl)-as-triazino[4,3-a][1,4-benzodiazepin-1(5H)-one.

EXAMPLE 79

7-Chloro-2-[(1-(t-butoxycarbonyl)ethylidene]-hydrazino]-5-(2,6difluorophenyl)-3H-1,4-benzodiazepine.

In the manner given in Example 1, 7-chloro-2-hydrazino-5-(2,6-difluorophenyl)-3H-1,4-benzodiazepine can be stirred with tert.-butyl pyruvate to give 7-chloro-2-[[1-(t-butyoxycarbonyl)ethylidene]hydrazino]-5-(2,6-difluorophenyl)-3H-1,4-benzodiazepine.

EXAMPLE 80

9-Chloro-2-methyl-7-(2,6-difluorophenyl)-as-triazino[4,3-a][1,4]benzodiazepin-1(5H)-one.

In the manner given in Example 6, a solution of 9-chloro-2-[[1-(t-butoxycarbonyl)ethylidene]hydrazino]-5-(2,6-difluorophenyl)-3H-1,4-benzodiazepine, in acetic acid, can be heated to reflux to give 9-chloro-2-methyl-7-(2,6-difluorophenyl)-as-triazino[4,3-a][1,4]benzodiazepin-1(5H)-one.

EXAMPLE 81

2-[[1-Carboxy-3-(dimethylamino)propylidene]-hydrazino]-5-phenyl-3H-1,4-benzdiazepine In the manner given in Example 13, 2-hydrazino-5-phenyl-3H-1,4-benzodiazepine can be stirred with 4-(dimethylamino)-2-oxobutyric acid at room temperature to give 2-[[1-carboxy-3-(dimethylamino)- propylidene]hydrazino]-5-phenyl-3H-1,4-benzodiazepine.

EXAMPLE 82

2-[[1-(Methoxycarbonyl)-3-(dimethylamino)-propylidene]hydrazino]-5-phenyl-3H-1,4-benzodiazepine In the manner given in Example 14, 2-[[1-carboxy-3-(dimethylamino)propylidene]hydrazino]-5-phenyl-3H-1,4-benzodiazepine can be treated with ethereal diazomethane to give 2-[[1-(methoxycarbonyl)-3-(dimethylamino)-propylidene]hydrazino]-5-phenyl-3H-1,4-benzodiazepine.

EXAMPLE 83

2-[2-(Dimethylamino)ethyl]-7-phenyl-as-triazino[4,3-a][1,4]benzodiazepin-1(5H)-one In the manner given in Example 15, a solution of 2-[[1-(methoxycarbonyl)-3-(dimethylamino)-propylidene]-hydrazino]-5-phenyl-3H-1,4-benzodiazepine in acetic acid can be heated to reflux to give 2-[2-(dimethylamino)-ethyl]-7-phenyl-as-triazino[4,3-a][1,4]benzodiazepin-1(5H)-one.

EXAMPLE 84

7-Chloro-2-[[1-carboxy-3-(dimethylamino)-propylidene]hydrazino]-5-(o-chlorophenyl)-3H-1,4-benzodiazepine In the manner given in Example 13, 7-chloro-2-hydrazino-5-(o-chlorophenyl)-3H-1,4-benzodiazepine can be stirred with 4-(dimethylamino)-2-oxobutanoic acid at room temperature to give 7-chloro-2-[[1-carboxy-3-(dimethylamino)propylidene]hydrazino]-5-(o-chlorophenyl)-3H-1,4-benzodiazepine.

EXAMPLE 85

7-Chloro-2-[[1-(methoxycarbonyl)-3-(dimethylamino)propylidene]hydrazino]-5-(o-chlorophenyl)-3H-1,4-benzodiazepine In the manner given in Example 14, 7-chloro-2-[[1-carboxy-3-(dimethylamino)propylidene]hydrazino]-5-(o-chlorophenyl)-3H-1,4-benzodiazepine can be treated with ethereal diazomethane to give 7-chloro-2-[[1-(methoxycarbonyl)-3-(dimethylamino)-propylidene]hydrazino]-5-(o-chlorophenyl)-3H-1,4-benzodiazepine.

EXAMPLE 86

9-Chloro-2-[2-(dimethylamino)ethyl]-7-(o-chlorophenyl)-as-triazino[4,3-a][1,4[benzodiazepin-1(5H)-one In the manner given in Example 15, a solution of 7-chloro-2-[[1-methoxycarbonyl)-3-(dimethylamino)-propylidene]hydrazino]-5-(o-chlorophenyl)-3H-1,4-benzodiazepine in acetic acid can be heated to reflux to give 9-chloro-2-[2-(dimethylamino)ethyl]-7-(o-chlorophenyl)-as-triazino-[4,3-a][1,4]benzodiazepin-1(5H)-one.

EXAMPLE 87

9-Chloro-2-[2-(dimethylamino)ethyl]-7-phenyl-as-triazino[4,3-a][1,4]benzodiazepin-1(5H)-one A stirred solution of tetramethyldiaminomethane (1.54 g., 0.015 mole) in dry dimethylformamide (75 ml.) was cooled in an ice bath while acetyl chloride (1.18 g., 0.015 mole) was added under nitrogen. The resulting slurry of dimethylmethylene ammonium chloride was allowed to reach ambient temperature and stirred for 20 minutes. The salt was allowed to settle and the dimethylformamide was removed via decantation under $N_2$. The salt was washed several times with fresh dimethylformamide and finally mixed with dimethylformamide (20 ml.). To this was slowly added 9-chloro-2-methyl-7-phenyl-as-triazino[4,3-a][1,4]benzodiazepine-1(5H)-one (3.37 g., 0.01 mole) under $N_2$. Upon mixing the reaction became homogeneous and after 1 hour the dimethylformamide solution was diluted with ethyl ether (300 ml.). The resulting slurry was filtered and the solid washed with ethyl ether. The residue was dissolved in methylene chloride and reprecipitated by adding the solution to ethyl ether. The solid was collected, washed with ethyl ether and dried to give 3.28 g., m.p. 155°–162° dec. of 9-chloro2-[2-(dimethylamino)ethyl]-7-phenyl-1-4H-triazino[4,3-a][1,4]benzodiazepin-1(5H)-one hydrochloride. The ir, uv and nmr of the free base supported the structure.

Anal. calcd. for $C_{21}H_{21}Cl_2N_5O$: C, 58.61; H, 4.92; Cl, 16.48; N, 16.28. Found: C, 53.29; H, 5.22; Cl, 17.82; N, 15.36; $H_2O$, 0.48.

EXAMPLE 88

7-Chloro-2-[[1-carboxy-4-(dimethylamino)-butylidene]hydrazino]-5-(o-chlorophenyl)-3H-1,4-benzodiazepine In the manner given in Example 13, 7-chloro-2-hydrazino-5-(o-chlorophenyl)-3H-1,4-benzodiazepine can be stirred with 5-(dimethylamino)-2-oxopentanoic acid at room temperature to give 7-chloro-2-[[1-carboxy-4-(dimethylamino)butylidene]hydrazino]-5-(o-chlorophenyl)-3H-1,4-benzodiazepine.

EXAMPLE 89

7-Chloro-2-[[1-(methoxycarbonyl)-4-(dimethylamino)butylidene]hydrazino]-5-(o-chlorophenyl)-3H-1,4-benzodiazepine In the manner given in Example 14, 7-chloro-2-[[1-carboxy-4-(dimethylamino)butylidene]hydrazino]-5-(o-chlorophenyl)-3H-1,4-benzodiazepine can be treated with ethereal diazomethane to give 7-chloro-2-[[1-(methoxycarbonyl)-4-(dimethylamino)-butylidene]hydrazino]-5-phenyl-3H-1,4-benzodiazepine.

EXAMPLE 90

9-Chloro-2-[3-(dimethylamino)propyl]-7-(o-chlorophenyl)-as-triazino[4,3-a][1,4]benzodiazepin-1(5H)-one In the manner given in Example 15, a solution of 7-chloro-2-[[1-methoxycarbonyl)-4-(dimethylamino)-butylidene]hydrazino]-5-(o-chlorophenyl)-3H-1,4-benzodiazepine in acetic acid can be heated to reflux to give 9-chloro-2-[3-(diethylamino)propyl]-7-(o-chlorophenyl)-as-triazino[4,3-a][1,4]benzodiazepin-1(5H)-one.

EXAMPLE 91

7-Chloro-2-[(1-carboxy-2-hydroxyethylidene)-hydrazino]-5-phenyl-3H-1,4-benzodiazepine In the manner given in Example 9, 7-chloro-2-hydrazino-5-phenyl-3H-1,4-benzodiazepine can be stirred with 3-hydroxy-2-oxopropionic at room temperature to give 7-chloro-2-[(1-carboxy-2-hydroxymethylidene)hydrazino]-5-(phenyl)-3H-1,4-benzodiazepine.

EXAMPLE 92

7-Chloro-2-[[1-(methoxycarbonyl)-2-hydroxyethylidene]hydrazino]-5-phenyl-3H-1,4-benzodiazepine In the manner given in Example 10, a solution of 7-chloro-2-[(1-carboxy-2-hydroxyethylidene)hydrazino]-5-phenyl-3H-1,4-benzodiazepine can be treated with ethereal diazomethane to give 7-chloro-2-[[1-(methoxycarbonyl)-2-hydroxyethylidene]hydrazino]-5-phenyl-3H-1,4-benzodiazepine.

EXAMPLE 93

9-Chloro-2-hydroxymethyl-7-phenyl-as-triazino[4,3-a][1,4]benzodiazepin-1(5H)-one In the manner given in Example 5, a solution of 7-chloro-2-[[1-(methoxycarbonyl)-2-hydroxyethylidene]-hydrazino]-5-(phenyl)-3H-1,4-benzodiazepine is heated to reflux with 1,2,4-trichlorobenzene to give 9-chloro-2-hydroxymethyl-7-phenyl-as-triazino[4,3-a][1,4-benzodiazepin-1(5H)-one.

EXAMPLE 94

9-Chloro-2-methyl-7-phenyl-as-triazino[4,3-a][1,4]benzodiazepin-1(5H)-one

To a solution of 7.09 g. (0.02 mole) of 7-chloro-2-[(1-carboxyethylidene)hydrazino]-5-phenyl-3H-1,4-benzodiazepine in 50 ml. of tetrahydrofuran, under nitrogen, was added with stirring 3.57 g. (0.0022 mole) of 1,1'-carbonyldiimidazole. After 30 minutes at 25° the mixture was stirred under reflux for 3 days and evaporated in vacuo. The residue was mixed with aqueous sodium bicarbonate and extracted with methylene chloride. The extract was washed with water, dried over sodium sulfate, filtered and evaporated in vacuo. The residue was crystallized from ethyl acetate giving 2.43 g. of 9-chloro-2-methyl-7-phenyl-as-triazino[4,3-a][1,4]-benzodiazepin-1(5H)-one, m.p. 193°-197°. An additional 1.29 g. (total yield 55%) was obtained from the filtrate by crystallization from ethyl acetate-hexane.

In the manner given in the prior examples other compounds of formula IV can be made. Representative compounds thus obtained include:
9-nitro-2-methyl-7-(2-pyridyl)-as-triazino[4,3-a][1,4]-benzodiazepin-1(5H)-one;
9-chloro-2,5-dimethyl-7-(2-pyridyl)-as-triazino[4,3-a]-[1,4]benzodiazepin-1(5H)-one;
9-chloro-2-methyl-7-(2-pyridyl)-as-triazino[4,3-a][1,4]-benzodiazepin-1(5H)-one;
9-(trifluoromethyl)-2-ethyl-7-(2-pyridyl)-as-triazino-[4,3-a][1,4]benzodiazepin-1(5H)-one;
9-fluoro-2-methyl-7-(2pyridyl)-as-triazino 4,3-a][1,4]-benzodiazepin-1(5H)-one;
10-nitro-2-hydroxymethyl-7-(o-chlorophenyl)-as-triazino-[4,3-a][1,4]benzodiazepin-1(5H)-one;
11-bromo-2-(3-hydroxypropyl)-7-(o-chlorophenyl)-as-triazino[4,3-a][1,4]benzodiazepin-1(5H)-one;
8-chloro-2-[(diethylamino)ethyl]-7-(o-fluorophenyl)-as-triazino[4,3-a][1,4]benzodiazepin-1(5H)-one;
8-nitro-5-methyl-2-[(diethylamino)methyl]-7-(p-chlorophenyl)-as-triazino[4,3-a][1,4]benzodiazepin-1(5H)-one;
9-fluoro-5-ethyl-2-[3-(diethylamino)propyl]-7-(m-fluorophenyl)-as-triazino[4,3-a][1,4]benzodiazepine-1(5H)-one;
9-nitro-2-[3-(dipropylamino)propyl]-7-(2,6-difluorophenyl)-as-triazino[4,3-a][1,4]benzodiazepin-1(5H)-one;
10-(trifluoromethyl)-2-[(3-(morpholino)propyl]-7-o-chlorophenyl-as-triazino[4,3-a][1,4benzodiazepin-1(5H)-one;
8-bromo-2-(2-pyrrolidinomethyl)-7-phenyl-as-triazino-[4,3-a][1,4benzodiazepin-1(5H)-one;
10-bromo-2-(3-pyrrolidinopropyl)-7-(o-fluorophenyl)-as-triazino[4,3-a][1,4benzodiazepin-1(5H)-one;
8-fluoro-2-(2-pyrrolidinoethyl)-7-(m-chlorophenyl)-as-triazino[4,3-a][1,4]benzodiazepin-1(5H)-one;
10-fluoro-7-(o-chlorophenyl)-as-triazino[4,3-a][1,4]-benzodiazepine-1(5H)-one;
2-(2-pyrrolidinoethyl)-7-(o-chlorophenyl)-as-triazino-[4,3-a][1,4]benzodiazepin-1(5H)-one;
2-(3-hydroxypropyl)-7-(o-chlorophenyl)-as-triazino-[4,3-a][1,4]benzodiazepin-1(5H)-one;
2-(hydroxymethyl)-7-(o-fluorophenyl)-as-triazino[4,3-a]-[1,4]benzodiazepin-1(5H)-one;
9-fluoro-2-allyl-7-(o-chlorophenyl)-as-triazino[4,3-a][1,4]benzodiazepin-1-(5H)-one;
9-nitro-2-allyl-7-(2,6-difluorophenyl)-as-triazino[4,3-a][1,4]benzodiazepin-1(5H)-one;
and the like.

In preparing the compounds of formula IV above, the intermediates of formula III are obtained. Representative compounds thus obtained include:
7-nitro-2-[[1-(methoxycarbonyl)ethylidene]hydrazino]-5-(2-pyridyl)-3H-1,4-benzodiazepine;
7-bromo-2-[[1-(methoxycarbonyl)ethylidene]hydrazino]-5-(2-pyridyl)-3H-1,4-benzodiazepine;
7-(trifluoromethyl)-2-[[1-(methoxycarbonyl)propylidene]hydrazino]-5-(2-pyridyl)-3H-1,4-benzodiazepine;
7-fluoro-2-[[1-(methoxycarbonyl)ethylidene]hydrazino]-5-(2-pyridyl)-3H-1,4-benzodiazepine;
8-nitro-2-[[1-(methoxycarbonyl)-2-hydroxyethylidene]hydrazino]-5-(o-chlorophenyl)-3H-1,4-benzodiazepine;
9-bromo-2-[[1-(methoxycarbonyl)-4-hydrxoybutylidene]hydrazino]-5-(o-chlorophenyl)-3H-1,4-benzodiazepine;
6-chloro-2-[[1-(methoxycarbonyl)-4-(dimethylamino)butylidene]hydrazino]-5-(o-fluorophenyl)-3H-1,4-benzodiazepine;
6-nitro-2-[[1-methoxycarbony)-2-(diethylamino)ethylidene]hydrazino]-3-methyl-5-(p-chlorophenyl)-3H-1,4-benzodiazepine;
7-fluoro-2-[[1-(methoxycarbonyl)-4-(diethylamino)-butylidene]hydrazino]-3-ethyl-5-(m-fluorophenyl)-3H-1,4-benzodiazepine;
7-nitro-2-[[1-(methoxycarbonyl)-4-(dipropylamino)-butylidene]hydrazino]-5-(2,6-difluorophenyl)-3H-1,4-benzodiazepine;
8-(trifluoromethyl)-2-[[1-(methoxycarbonyl)-4-morpholinobutylidene]hydrazino]-5-(o-chlorophenyl)-3H-1,4-benzodiazepine;
6-bromo-2-[[1-(methoxycarbonyl)-3-pyrrolidinopropylidene]hydrazino]-5-phenyl-3H-1,4-benzodiazepine;
8-bromo-2-[[1-(methoxycarbonyl)-4-pyrrolidinobutylidene]hydrazino]-5-(o-fluorophenyl)-3H-1,4-benzodiazepine;

6-fluoro-2-[[1-(methoxycarbonyl)-3-pyrrolidinopropylidene]hydrazino]-5-(m-chlorophenyl)-3H-1,4-benzodiazepine;
8-fluoro-2-[[1-(methoxycarbonyl)ethylidene]hydrazino]-5-(o-chlorophenyl)-3H-1,4-benzodiazepine;
2-[[1-(methoxycarbonyl)-3-pyrrolidinopropylidene]hydrazino]-5-(o-chlorophenyl)-3H-1,4-benzodiazepine;
2-[[1-(methoxycarbonyl)-4-hydroxypropylidene]hydrazino]-5-(o-chlorophenyl)-3H-1,4-benzodiazepine;
2-[[1-(methoxycarbonyl)-2-hydroxyethylidene]hydrazino]-5-(o-fluorophenyl)-3H-1,4-benzodiazepine;
7-fluoro-2-[[1-(methoxycarbonyl)-3-butenylidene]hydrazino]-5-(o-chlorophenyl)-3H-1,4-benzodiazepine;
7-nitro-2-[[1-[(p-nitrophenoxy)carbonyl]-3-butenylidene]hydrazino]-5-(2,6-difluorophenyl)-3H-1,4-benzodiazepine;
7-chloro-2-[[(methoxycarbonyl)methylene]hydrazino]-5-(2-pyridyl)-3H-1,4-benzodiazepine;
and the like.

the pharmacologically acceptable acid addition salts of compounds of formulae III or IV (as well as of formula IVA and IVB) can be prepared and isolated by conventional processes, such as reacting a compound of formula II with a selected pharmacologically acceptable acid. Such acids, include hydrochloric, hydrobromic, phosphoric, sulfuric, acetic, tartaric, lactic, citric, malic, maleic, methanesulfonic, benzenesulfonic, cyclohexanesulfamic acids, toluenesulfonic, and the like. The reaction is conveniently performed in an organic solvent, e.g., ether, dioxane or tetrahydrofuran, ethanol, methanol, ethyl acetate; the salts can be recovered by crystallization, precipitation or evaporating the solvent. These salts are useful in the same manner as the free base.

I claim:
1. An as-triazinobenzodiazepin-1-one of the formula IV

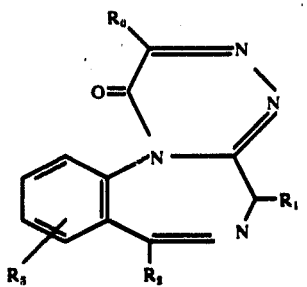

where in $R_0$ is hydrogen, alkyl of 1 to 3 carbon atoms, inclusive, —$C_nH_{2n}OR$, in which $n$ is an integer of 1 to 3, inclusive, and R is hydrogen or methyl,

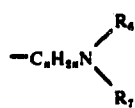

in which $n$ is defined as before and $R_6$ and $R_7$ are hydrogen or alkyl as defined above, or together

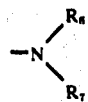

is pyrrolidino, piperidino, morpholino, or

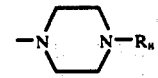

in which $R_8$ is methyl, ethyl, or 2-hydroxyethyl,

in which $m$ is an integer of 0 to 3 inclusive, and $R_9$ is hydrogen, lower alkyl of from 1 to 4 carbon atoms, inclusive; wherein $R_1$ is hydrogen or methyl; wherein $R_2$ is phenyl, o-chlorophenyl, o-fluorophenyl, 2,6-difluorophenyl or 2-pyridyl; and wherein $R_3$ is hydrogen, chloro, fluoro, bromo, trifluoromethyl, or nitro, or the pharmacologically acceptable acid addition salts thereof.

2. A compound according to claim 1 of the formula IVA

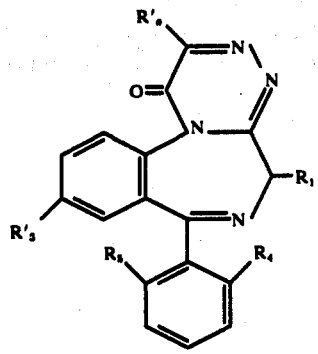

wherein $R'_0$ is hydrogen, alkyl of 1 to 3 carbons atoms, inclusive, —$C_nH_{2n}OH$, in which $n$ is an integer of 1 to 3 inclusive, or

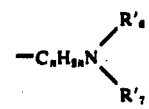

in which $n$ is defined as above and $R'_6$ and $R'_7$ are alkyl of one to three carbon atoms, inclusive; wherein $R_1$ is hydrogen or methyl; wherein $R'_3$ is hydrogen, fluoro, or chloro; wherein $R_4$ is hydrogen, fluoro, or chloro; and wherein $R_5$ is hydrogen or fluoro with the proviso that $R_5$ is not fluoro if $R_4$ is chloro, and the pharmacologically acceptable acid addition salts thereof.

3. A compound according to claim 1 of the formula IVB:

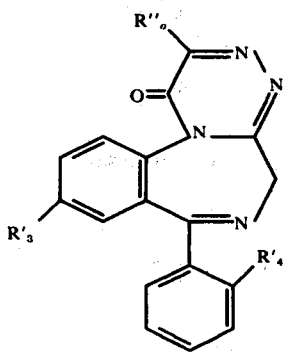

wherein $R''_o$ is hydrogen, methyl, hydroxmethyl, or

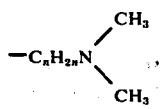

in which $n$ is an integer of 1 to 3, inclusive; wherein $R'_3$ is hydrogen, chloro, or fluoro; and wherein $R'_4$ is hydrogen or chloro, and the pharmacologically acceptable acid addition salts thereof.

4. A compound according to claim 3 wherein $R''_o$ is methyl; $R'_3$ is chloro; $R'_4$ is hydrogen; and the compound is therefore 9-chloro-2-methyl-7-phenyl-as-triazino-[4,3-a][1,4]benzodiazepin-1(5H)-one.

5. A compound according to claim 3, wherein $R''_o$ is methyl, $R'_3$ and $R'_4$ are chloro and the compound is therefore 9-chloro-2-methyl-7-(o-chlorophenyl)-as-triazino[4,3-a][1,4]benzodiazepine-1(5H)-one.

6. A compound according to claim 3, wherein $R''_o$ is methyl; $R'_3$ is hydrogen; $R'_4$ is chloro, and the compound is therefore 2-methyl-7-(o-chlorophenyl)-as-triazino[4,3-a][1,4]benzodiazepin-1(5H)-one.

7. A compound according to claim 3, wherein $R''_o$ is hydrogen, $R'_3$ is chlorine, $R'_4$ is hydrogen, and the compound is therefore 9-chloro-7-phenyl-as-triazino[4,3-a][1,4]benzodiazepin-1(5H)-one.

8. A compound according to claim 3, wherein $R''_o$ is (dimethylamino)methyl, $R'_3$ is chloro and $R'_4$ is hydrogen and the compound is therefore 9-chloro-2-[(dimethylamino)-methyl]-7-phenyl-as-triazino[4,3-a]1,4]benzodiazepin-1(5H)-one.

9. A compound according to claim 3, wherein $R''_o$ is 2-(dimethylamino)ethyl, $R'_3$ is chloro and $R'_4$ is hydrogen, and the compound is therefore 9-chloro-2-[2-(dimethylamino)ethyl]-7-phenyl-as-triazino[4,3-a][1,4]-benzodiazepin-1(5H)-one.

10. A compound according to claim 3, wherein $R''_o$ is carbomethoxyethyl, $R'_3$ is chlorine, $R'_4$ is hydrogen, and the compound is therefore 9-chloro-2-carbomethoxyethyl-7-phenyl-as-triazino[4,3-a]1,4]benzodiazepin-1(5H)-one.

11. A compound according to claim 3, wherein $R''_o$ is hydroxymethyl; wherein $R'_3$ and $R'_4$ are chloro, and the compound is therefore 9-chloro-2-(hydroxymethyl)-7-(o-chlorophenyl)-as-triazino[4,3-a][1,4]benzodiazepin-1(5H)-one.

12. A compound according to claim 3, wherein $R''_o$ is (diethylamino)propyl, $R'_3$ is chloro, and $R'_4$ is hydrogen, and the compound is therefore 9-chloro-2-[(diethylamino)propyl]-7-phenyl-as-triazino[4,3-a][1,4]benzodiazepin-1(5H)-one.

* * * * *

UNITED STATES PATENT AND TRADEMARK OFFICE
CERTIFICATE OF CORRECTION

PATENT NO. : 4,017,492
DATED : April 12, 1977
INVENTOR(S) : Robert B. Moffett

It is certified that error appears in the above-identified patent and that said Letters Patent are hereby corrected as shown below:

Column 32, line 2, "diazepine" should read -- diazepin --
line 15, "[4,3-a]1,4]" should read -- [4,3-a][1,4] --
line 24, "[4,3-a]1,4]" should read -- [4,3-a][1,4] --

Signed and Sealed this

Twenty-sixth Day of June 1979

[SEAL]

Attest:

RUTH C. MASON
Attesting Officer

DONALD W. BANNER
Commissioner of Patents and Trademarks